United States Patent [19]

Klimko et al.

[11] Patent Number: 5,807,892
[45] Date of Patent: Sep. 15, 1998

[54] USE OF CERTAIN PROSTAGLANDIN ANALOGUES TO TREAT GLAUCOMA AND OCULAR HYPERTENSION

[75] Inventors: Peter G. Klimko; Robert D. Selliah, both of Ft. Worth; Thomas R. Dean, Weatherford; Mark R. Hellberg, Arlington, all of Tex.; John E. Bishop, Groton, Mass.

[73] Assignee: Alcon Laboratories, Inc., Fort Worth, Tex.

[21] Appl. No.: 480,706

[22] Filed: Jun. 7, 1995

Related U.S. Application Data

[63] Continuation-in-part of Ser. No. 316,672, Sep. 30, 1994, abandoned.

[51] Int. Cl.$^6$ .......................... A61K 31/695; A61K 31/35; C07C 177/00
[52] U.S. Cl. ..................... 514/530; 514/573; 514/729; 560/121
[58] Field of Search ................................... 514/530, 573; 514/729; 560/121

[56] References Cited

U.S. PATENT DOCUMENTS

| | | |
|---|---|---|
| 4,444,788 | 4/1984 | Skuballa et al. . |
| 4,454,339 | 6/1984 | Skuballa et al. . |
| 4,789,685 | 12/1988 | Skuballa et al. . |
| 4,824,857 | 4/1989 | Goh et al. . |
| 4,883,819 | 11/1989 | Bito . |
| 5,001,153 | 3/1991 | Ueno et al. . |
| 5,004,752 | 4/1991 | Raduechel et al. . |
| 5,057,621 | 10/1991 | Cooper et al. . |
| 5,079,259 | 1/1992 | Skuballa et al. . |
| 5,093,329 | 3/1992 | Woodward . |
| 5,151,444 | 9/1992 | Ueno et al. . |
| 5,194,429 | 3/1993 | Ueno et al. . |
| 5,204,371 | 4/1993 | Skuballa et al. . |
| 5,296,504 | 3/1994 | Stjernschantz et al. . |
| 5,302,617 | 4/1994 | Ueno . |
| 5,446,041 | 8/1995 | Chan et al. . |

FOREIGN PATENT DOCUMENTS

| | | |
|---|---|---|
| B-88726/91 | 6/1994 | Australia . |
| 0 253 094 A2 | 1/1988 | European Pat. Off. . |
| 0 299 914 B1 | 7/1988 | European Pat. Off. . |
| 0 330 511 A2 | 8/1989 | European Pat. Off. . |
| 0 364 417 A1 | 4/1990 | European Pat. Off. . |
| 0 435 682 A2 | 7/1991 | European Pat. Off. . |
| 0 561 073 A1 | 9/1993 | European Pat. Off. . |
| 40 36 140 A1 | 5/1992 | Germany . |
| 42 29 048 A1 | 3/1994 | Germany . |
| 42 29 050 A1 | 3/1994 | Germany . |
| 42 29 051 | 3/1994 | Germany . |
| WO 85/04656 | 10/1985 | WIPO . |
| WO 86/04504 | 8/1986 | WIPO . |
| WO 90/02553 | 3/1990 | WIPO . |
| WO 92/08697 | 5/1992 | WIPO . |
| 9405631 A1 | 3/1994 | WIPO . |
| WO 95/18101 | 7/1995 | WIPO . |

OTHER PUBLICATIONS

Braun, et al., "Effect of ZK 110.841 on Cerebral Vascular Contraction and TXA$_2$–Release Caused by Thrombin–Stimulated Platelets," *Archives of Pharmacology*, 339 Suppl:R37(148)(1989).

Buchmann et al., "Synthesis of a Chemical and Metabolically Stable and Biologically Potent PGD$_2$–Analogue," *Tetrahedron Letters*, 31(24):3425–3428(1990).

Bundy, et al., "Synthesis and Platelet Aggregation Inhibiting Activity of Prostaglandin D Analogues" *J. Med. Chem.* 26(6):790–799(1983).

Goh et al., *Graefe's Arch. Clin. Exp. Ophthalmol.*, 227:476–481 (1989).

Nakajima et al., *Graefe's Arch. Clin. Exp. Ophthalmol.*, 229:411–413(1991).

"New Research Drug DLO/8419" Drug License Opportunities (IMSWorld Publications)(Jun. 25, 1990).

Ney, "Potent Inhibition of FMLP–Induced Neutrophil Activation by the PGD$_2$ Analogue ZK 110.841," *Archives of Pharmacology*, 339 Suppl:R38 (150)(1989).

Thierauch et al., *Prostaglandins*, 35:6:855–868 (1988).

Thierauch et al., *Advances in Prostaglandin. Thromboxane and Leukotriene Research*, 19:655–658 (1989).

Woodward et al., *Invest. Ophthalmol. Vis. Sci.*, 31:138–146 (1990).

*Derwent* Abstract No. 92–168152/21 for DE 4036140–A, May 1992.

*Primary Examiner*—Paul J. Killos
*Attorney, Agent, or Firm*—Barry L. Copeland

[57] ABSTRACT

Certain prostaglandin analogues are useful in the treatment of glaucoma and ocular hypertension. Also disclosed are ophthalmic, pharmaceutical compositions comprising such prostaglandin analogues.

19 Claims, No Drawings

USE OF CERTAIN PROSTAGLANDIN ANALOGUES TO TREAT GLAUCOMA AND OCULAR HYPERTENSION

The present application is a continuation-in-part of U.S. patent application Ser. No. 08/316,672 filed Sep. 30, 1994, now abandoned.

BACKGROUND OF THE INVENTION

The present invention relates to the use of certain prostaglandin analogues for the treatment of glaucoma and ocular hypertension As used herein, the terms "prostaglandin" and "PG" shall refer to prostaglandins and derivatives and analogues thereof, except as otherwise indicated by context.

Naturally-occurring prostaglandins are known to lower intraocular pressure (IOP) after topical ocular instillation, but generally cause inflammation, as well as surface irritation characterized by conjunctival hyperemia and edema. Many synthetic prostaglandins have been observed to lower intraocular pressure, but such compounds also produce the aforementioned side effects. Various methods is have been used in attempting to overcome the ocular side effects associated with prostaglandins. Stjernschantz et al. (EP 364 417 B1) have synthesized derivatives or analogues of naturally-occurring prostaglandins in order to design out selectively the undesired side effects while maintaining the IOP-lowering effect. Buchmann et al. (WO 94/05631) discloses certain species of 9-chloro-prostaglandin esters and amides said to be suitable for lowering intraocular pressure. Others, including Ueno et al. (EP 330 511 A2) and Wheeler (EP 435 682 A2) have tried complexing prostaglandins with various cyclodextrins.

SUMMARY OF THE INVENTION

It has now been unexpectedly discovered that certain D series prostaglandin analogues are significantly more effective in lowering IOP than other, known prostaglandins. In particular, the prostaglandin analogues of the present invention have unexpectedly been found to lower IOP to a greater degree than most other known PGs and without the side effects typically associated with inflammation which often accompany topical ocular administration of D series prostaglandins.

DETAILED DESCRIPTION OF THE INVENTION

The prostaglandins which are useful in the compositions of the present invention have the general formula:

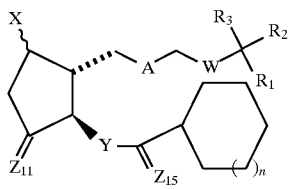
(I)

wherein:

$R_1$=$CH_2R$, $CO_2R_4$;

R=OH or functionally modified (i.e., etherified and acylated) hydroxy group;

$R_2$ and $R_3$ can be the same or different and are selected from: H and $CH_3$;

$R_4$32 H, a cationic salt moiety, substituted or unsubstituted alkyl, cycloalkyl, (cycloalkyl)alkyl, aryl, arylalkyl, heteroaryl, or (heteroaryl)alkyl, wherein substituents include alkyl, halo, a free or functionally modified hydroxy group or a free or functionally modified thiol;

W=$CH_2$, O, $S(O)_m$ wherein m=0, 1, 2;

A=$CH_2CH_2$, cis or trans CH=CH, or C≡C;

X=Cl, F or R in either configuration, or H;

$Z_{11}$ and $Z_{15}$ may be the same or different and may be selected from O (i.e., a carbonyl) or H and R in either configuration;

Y=$CH_2CH_2$ or trans CH=CH, or C≡C; and n=0 or 1.

It is preferred to use compounds of formula (I) wherein: W=$CH_2$ or O; A =cis CH=CH; X=Cl or H; $Z_{11}$=R and H in either configuration; Y=$CH_2CH_2$, or trans CH=CH; and n=1. It is most preferred to use such compounds of formula (I) wherein: $R_2$, $R_3$ =H; X=Cl in β-configuration, or H; $Z_{15}$=H and R in either configuration; $R_1$=$CO_2R_4$ and $R_4$=H, a cationic salt moiety, or substituted or unsubstituted $C_1$–$C_{10}$ alkyl.

Some of the compounds of formula (I) are novel. The novel compounds of formula (I) are those wherein: $R_1$=$CH_2R$, $CO_2R_4$; R=OH or functionally modified (i.e., etherified and acylated) hydroxy group; $R_2$ and $R_3$ can be the same or different and are selected from: H and $CH_3$; $R_4$=H, a cationic salt moiety, substituted or unsubstituted alkyl, cycloalkyl, (cycloalkyl)alkyl, aryl, arylalkyl, heteroaryl, or (heteroaryl)alkyl, wherein substituents include alkyl, halo, a free or functionally modified hydroxy group or a free or functionally modified thiol; W=O, $S(O)_m$ wherein m=0, 1, 2; A=$CH_2CH_2$, cis or trans CH=CH, or C≡C; X=H; $Z_{11}$ and $Z_{15}$ may be the same or different and may be selected from O (i.e., a carbonyl) or H and R in either configuration; Y=$CH_2CH_2$ or trans CH=CH, or C≡C; and n=0 or 1.

The preferred novel compounds are those of formula (I) wherein: $R_1$=$CO_2R_4$; $R_2$ and $R_3$=H; $R_4$=H, a cationic salt moiety, or a substituted or unsubstituted $C_1$–$C_{10}$ alkyl; W=O, A=cis CH=CH; $Z_{11}$=R and H in either configuration; Y=$CH_2CH_2$, or trans CH=CH; $Z_{11}$=H and R in either configuration; and n=0 or 1.

The following Table 1 contains examples of some preferred compounds of the present invention.

TABLE 1

| | COMPOUND NAME | COMPOUND STRUCTURE |
|---|---|---|
| II | (5Z)-(9R, 11R, 15R)-9-Chloro-15-cyclohexyl-11-hydroxy-15-methoxy-3-oxa-16,17,18,19,20-pentanor-5-prostenoic acid t-butyl ester | 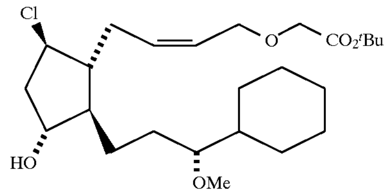 |
| III | (5E)-(11R, 15R)-15-Cyclohexyl-11,15-dihydroxy-3-oxa-16,17,18,19,20-pentanor-5-prostenoic acid isopropyl ester | 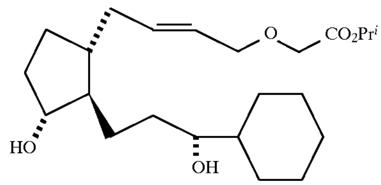 |
| IV | (5E, 13E)-(11R, 15S)-15-Cyclohexyl-11,15-dihydroxy-3-oxa-16,17,18,19,20-pentanor-5,13-prostadienoic acid isopropyl ester | 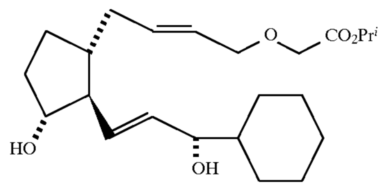 |
| V | (5Z)-(9R, 11R, 15R)-9-Chloro-15-cyclohexyl-11,15-dihydroxy-3-oxa-16,17,18,19,20-pentanor-5-prostenol | 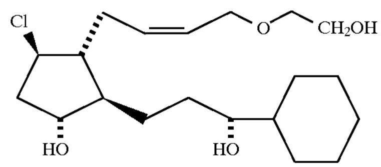 |
| VI | (5Z)-(9R, 11R, 15S)-9-Chloro-15-cyclohexyl-11,15-dihydroxy-3-oxa-6,17,18,19,20-pentanor-5,13-prostadienyl | 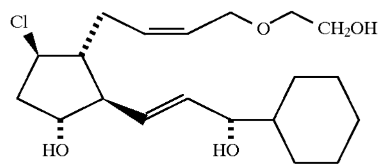 |
| VII | (5E, 13E)-(9R, 11R, 15S)-9-Chloro-15-cyclohexyl-11,15-dihydroxy-3-oxa-16,17,18,19,20-pentanor-5,13-prostadienoic acid t-butyl ester | 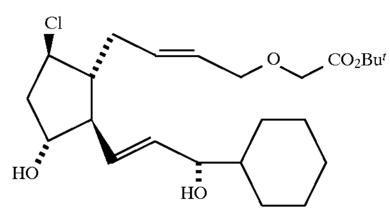 |
| VIII | (5Z)-(9R, 11R, 15S)-9-Chloro-15-cyclohexyl-11,15-dihydroxy-3-oxa-16,17,18,19,20-pentanor-5-prostenoic acid isopropyl ester | 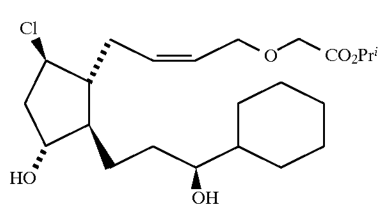 |
| IX | (5Z)-(9R, 11R, 15R)-9-Chloro-15-cyclohexyl-11,15-dihydroxy-3-oxa-16,17,18,19,20-pentanor-5-prostenoic acid neopentyl ester | 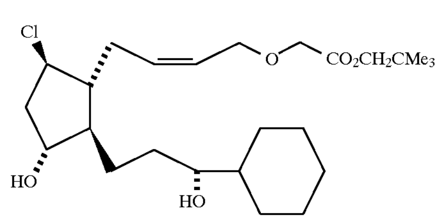 |

TABLE 1-continued

| COMPOUND NAME | COMPOUND STRUCTURE |
| --- | --- |
| X  (5Z, 13E)-(11R, 15S)-15-Cyclohexyl-11,15-dihydroxy-3-oxa-16,17,18,19,20-pentanor-5,13-prostadienoic acid isopropyl ester | |

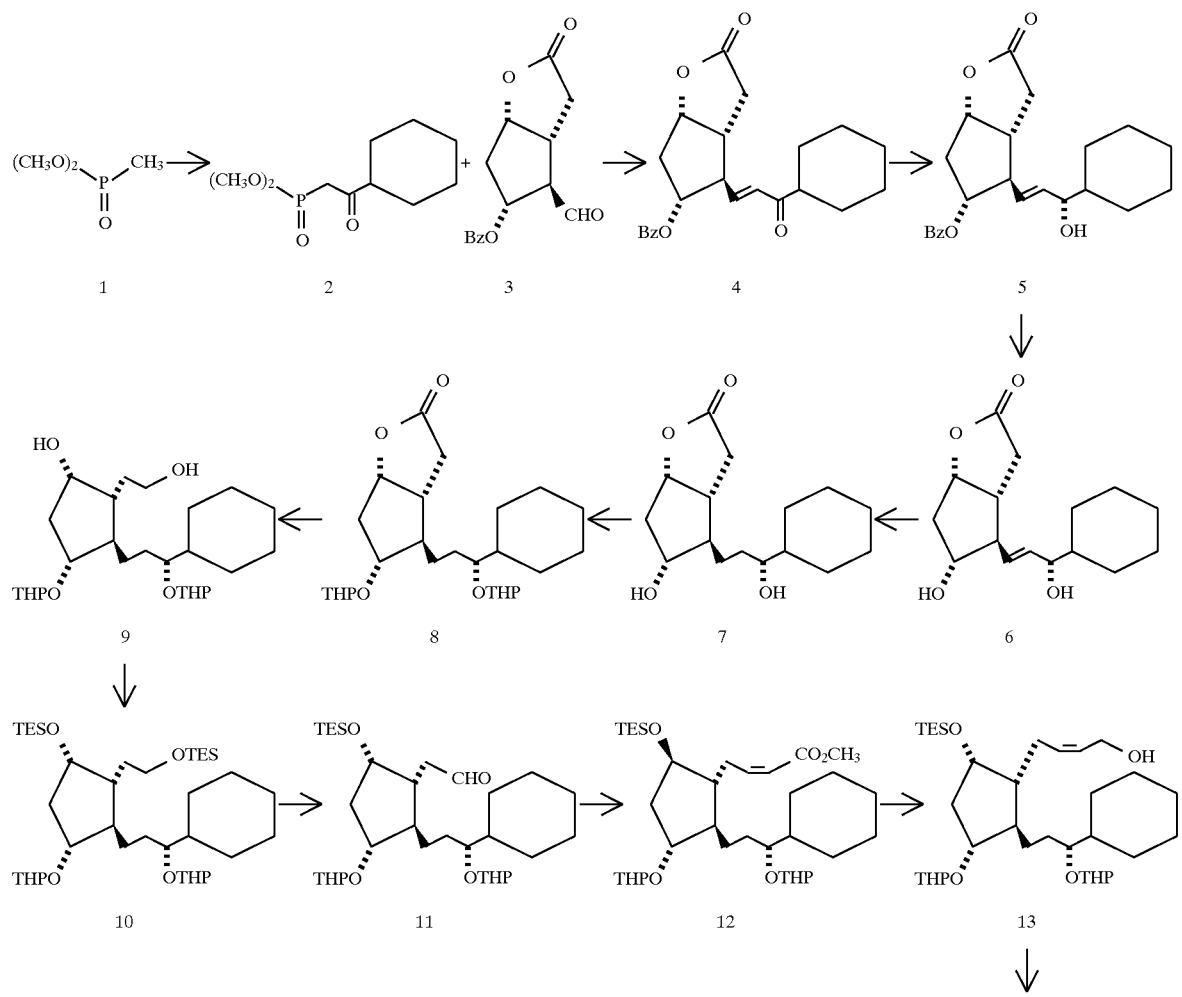

In the following Examples 1–11, the following standard abbreviations are used: g=grams (mg=milligrams and μg=micrograms); mol=moles (mmol=millimoles); mL=milliliters; mm Hg=millimeters of mercury; mp=melting point; bp=boiling point; h=hours; and min=minutes. In addition, "NMR" refers to nuclear magnetic resonance spectroscopy and "CI MS" refers to chemical ionization mass spectrometry.

EXAMPLE 1

SYNTHESIS OF COMPOUND II

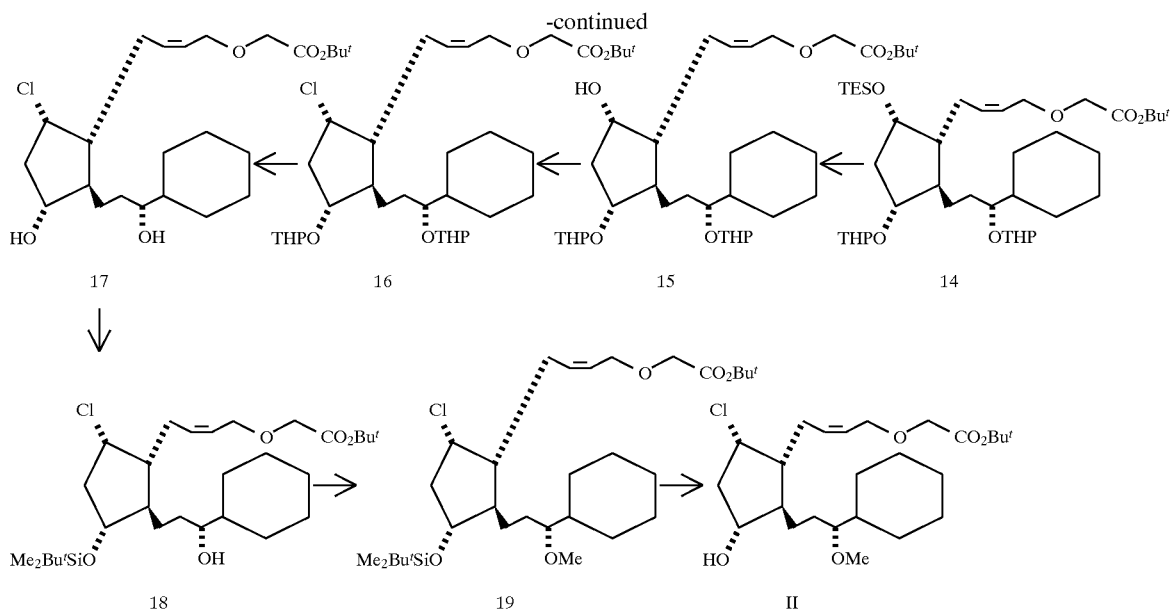

A: Dimethyl (2-cyclohexyl-2-oxo)ethylphosphonate (2):

A solution of dimethyl methylphosphonate (100 g, 0.8 mol) in 1.0 L of anhydrous THF was cooled to −70° C. and n-BuLi (2.5M in hexanes, 320 mL, 0.8 mol) was added dropwise such that the temperature remained below −60° C. The mixture was stirred for 10 min at −70° C. and then methyl cyclohexanecarboxylate (57.3 mL, 0.4 mol) was added dropwise, via syringe, over a period of 15 min. The resulting mixture was then stirred for 14 h at room temperature. The reaction was quenched by first cooling to 0° C. followed by the addition of 2M HCl until the aqueous layer was at pH 2. The layers were separated and the aqueous layer was extracted with 2×200 mL of $CH_2Cl_2$. The organic layers were combined and washed sequentially with 200 mL each of water and brine and then dried ($MgSO_4$). Filtration and solvent removal gave a yellow oil which was distilled under vacuum to afford 67.3 g (72%) of 2 as a dear colorless liquid: bp 100°–115° C. (0.01 mmHg); $^1$H NMR ($CDCl_3$) δ 3.74 (d, J=12.0 Hz, 6H), 3.08 (d, J=22 Hz, 2H), 2.55 (m, 1H), 1.95–1.60 (m, 5H), 1.40–1.15 (m, 5H).

B: (3aR, 4R, 5R, 6aS)-5-(Benzoyloxy)4-[(E)-3-cyclohexyl-3-oxo-1-propenyl]-hexahydro-2H-cyclopenta[b]furan-2-one (4):

A solution of anhydrous THF (1.4 L), LiCl (11.7 g, 0.28 mol) and the phosphonate 2 (67.0 g, 0.28 mol) was cooled to 0° C. and triethylamine (39.2 mL, 0.28 mol) was added dropwise. A solution of the aldehyde 3 (68.5 g, 0.25 mol) in dry $CH_2Cl_2$ (320 mL) was added dropwise to the cold suspension and the resulting mixture was stirred at 0° C. for 3 h. The reaction mixture was then poured into 500 mL of 2M HCl, and layers were separated. The aqueous layer was extracted with 500 mL of $CH_2Cl_2$. Combined organic layers were washed with 100 mL each of water and brine followed by drying over $MgSO_4$. Filtration and solvent removal gave a yellow solid which was recrystallized from EtOAc to afford 85.8 g (89%) of 4 as a white solid: mp 151°–153° C.; $^1$H NMR ($CDCl_3$) δ 8.01 (d, J=2.0 Hz, 2H), 7.65–7.40 (m, 3H), 6.70 (dd, J=12, 6 Hz, 1H), 6.35 (d, J=12 Hz, 1H), 5.32 (m, 1H), 5.15 (m, 1H), 2.93 (m, 3H), 2.72–2.25 (m, 4H), 1.85–1.56 (m, 6H), 1.40–1.15 (m, 5H).

C: (3aR, 4R, 5R, 6aS)-5-(Benzoyloxy)-4-[(E)-(3S)-3-cyclohexyl-3-hydroxy-1-propenyl]-hexahydro-2H-cyclopenta[b]furan-2-one (5):

A solution of $CeCl_3 \cdot 7H_2O$ (19.5 g, 52.3 mmol) and enone 4 (20.0 g, 52.3 mmol) in 150 mL of $CH_3OH$ and 70 mL of $CH_2Cl_2$ was prepared. $NaBH_4$ (1.92 g, 52.3 mmol) was added in small portions over a period of 5 min. The resulting mixture was stirred at ambient temperature for 45 min and then was poured into a separatory funnel containing 100 mL each of 25% (v/v) aqueous acetic acid and $CH_2Cl_2$. Layers were separated and the aqueous layer was extracted with 3×50 mL of $CH_2Cl_2$. Combined organic layers were washed with sat. $NaHCO_3$ (50 mL), and brine (50 mL), and then dried ($MgSO_4$). Upon solvent removal, 23.7 g of a colorless oil containing nearly equal amounts of the two diastereomeric allyl alcohols was obtained. Diastereomers were separated by HPLC (40% EtOAc/hexane), affording 5 (9.34 g (46%), the less polar component) as a white solid. $^1$H NMR ($CDCl_3$) δ 8.01 (d, J=8 Hz, 2H), 7.62–7.28 (m, 3H), 5.61 (m, 2H), 5.25 (m, 1H), 5.08 (m, 1H), 3.85 (m, 1H), 2.95–2A5 (m, 5H), 2.30 (m, 2H), 1.95–1.55 (m, 6H), 1.50–0.80 (m, 5H).

D: (3aR, 4R, 5R, 6aS)4-[(3R)-3-Cyclohexyl-3-hydroxypropyl]-hexahydro-5-hydroxy-2-H-cyclopenta[b]furan-2-one (7):

A solution of the allyl alcohol 5 (10.0 g, 26.0 mmol) in warm methanol (100 mL) was cooled to ambient temperature. Anhydrous $K_2CO_3$ (3.6 g, 26.0 mmol) was added and the resulting mixture was stirred at ambient temperature for 3 h. The reaction mixture was concentrated and the residue was partitioned between 100 mL each of EtOAc and 1M HCl. Layers were separated and the aqueous phase was extracted with 3×50 mL of EtOAc. Combined organic layers were washed with 50 mL of water, 2×50 mL of sat. $NaHCO_3$, 50 mL of brine, and dried over $MgSO_4$. Filtration and evaporation gave the diol 6 (9.8 g, 92% yield, $R_f$=0.26, 100% EtOAc), which was used in the subsequent reaction without further purification.

The crude diol 6 (9.8 g, 26 mmol) was dissolved in 50 mL of EtOAc and a catalytic amount (0.1 g) of 5% Pd/C was added. This mixture was hydrogenated at 30–40 psi in a Parr hydrogenation apparatus for 3 h and then filtered through a short pad of Celite. The filtrate was concentrated and the crude yellow oil was purified by passage through a short column of silica ($R_f$=0.26, EtOAc) to afford 7 (5.06 g, 70% yield from 5) as a colorless, viscous oil which solidified upon standing. $^1$H NMR (CDCl$_3$) δ 4.95 (m, 1H), 4.05 (m, 1H), 3.35 (m, 1H), 2.80 (m,1H), 2.58 (m, 2H), 2.30 (m, 1H), 2.00 (m, 14H).

E: (3aR, 4R, 5R, 6aS)-4-[(3R)-3-Cyclohexyl-3-(tetrahydropyran-2-yloxy)propyl]-hexahydro-5-(tetrahydropyran-2-yloxy)-2H-cyclopenta[b]furan-2-one (8):

A solution of the diol 7 (6.0 g, 21.2 mmol) and dihydropyran (7.80 mL, 84.8 mmol) in CH$_2$Cl$_2$ (100 mL) was cooled to 0° C. A catalytic amount of p-TsOH (0.05 g, 0.26 mmol) was added and the mixture was stirred for 30 min at 0° C. The reaction was then quenched by adding sat. aqueous NaHCO$_3$ (10 mL). Layers were separated and the aqueous phase was extracted with 2×25 mL of CH$_2$Cl$_2$. Combined organic layers were dried over anhydrous K$_2$CO$_3$, filtered and concentrated to afford a colorless oil which was purified by passage through a short column of silica (R$_f$=0.46, 1:1 EtOAc/hexanes). The bis-THP ether 8 (8.59 g, 89% yield) was isolated as a colorless oil which solidified upon standing. $^1$H NMR (CDCl$_3$) δ (characteristic peaks only) 5.00 (m, 1H), 4.75–4.45 (m, 2H), 3.85 (m, 2H), 3.60–3.30 (m, 4H).

F: (9S, 11R, 15R)-11,15-Bis-(tetrahydropyran-2-yloxy)-15-cyclohexyl-2,3,4,5,6,16,17,18,19,20-decanor-9-(triethylsilyloxy)prostanol Triethylsilyl Ether (10):

A suspension of lithium aluminum hydride (1.43 g, 38.0 mmol) in 50 mL of anhydrous THF was cooled to 0° C. and a solution of the lactone 8 (8.59 g, 19.0 mmol) in THF (100 mL) was added dropwise. The resulting mixture was stirred at 0° C. for 3 h after which 1.5 mL of H$_2$0, 1.5 mL 15% NaOH and 4.5 mL of H$_2$O were sequentially added. After warming to ambient temperature, 100 mL of EtOAc was added and solids were filtered off. The filter cake was washed thoroughly with 3×50 mL of EtOAc and the filtrates were dried by passage through a short pad anhydrous MgSO$_4$. Evaporation afforded 9 (9.02 g) as a colorless oil which was used in the subsequent step without further purification (R$_f$=0.31, 80:20 EtOAc/hexanes).

A mixture of the crude diol 9 (9.02 g, 19.0 mmol), triethylsilyl chloride (9.65 mL, 57.0 mmol), dimethylaminopyridine (0.41 g, 3.42 mmol), triethylamine (16.0 mL, 114 mmol) and anhydrous N,N-dimethylformamide (50 mL) was stirred at ambient temperature for 14 h under N$_2$. The reaction mixture was then diluted with 250 mL of CH$_2$Cl$_2$ and the solution was washed with 3×50 mL H$_2$O. Combined water washes were extracted with 2×50 mL of CH$_2$Cl$_2$. Organic layers were combined, dried (MgSO$_4$), filtered and concentrated to afford a yellow oil which was chromatographed on silica (R$_f$=0.4, 1:9 EtOAc/hexanes). Pure 10 (11.23 g, 86% yield from 8) was obtained as a slightly yellow oil. $^1$H NMR (CDCl$_3$) δ (characteristic peaks only) 4.62 (m, 2H), 4.15–3.25 (broad m, 7H), 2.30–1.15 (broad m, 18H), 0.95 (broad t, 18H), 0.65 (broad q, 12H).

G: (9S, 11R, 15R)-11,15-Bis-(tetrahydropyran-2-yloxy)-15-cyclohexyl-2,3,4,5,6,16,17,18,19,20-decanor-9-(triethylsilyloxy)prostanal (11):

A solution of oxalyl chloride (0.51 mL, 0.57 mmol) in anhydrous CH$_2$Cl$_2$ (15 mL) was cooled to −78° C. under N$_2$. A solution of anhydrous DMSO (0.81 mL, 11.4 mmol) in CH$_2$Cl$_2$ (2.0 mL) was then added dropwise. After 2 min, a solution of 10 (2.6 g, 3.8 mmol) in 8 mL of dry CH$_2$Cl$_2$ was introduced dropwise via syringe over a period of 2 min. The resulting mixture was stirred at −78° C. for 2 h at which time triethylamine (2.7 mL, 19.0 mmol) was added. The reaction was stirred for 15 min and then allowed to warm to ambient temperature. The mixture was partitioned between 100 mL of EtOAc and 10 mL of H$_2$O and the organic layer was washed with an additional 10 mL H$_2$O, 10 mL of brine and dried (MgSO$_4$). Solvent removal gave a yellow oil which was subjected to chromatography on silica gel (R$_f$=0.2, 10% EtOAc/hexanes) to afford 11 (1.4 g, 65% yield) and some starting material (0.83 g). $^1$H NMR (CDCl$_3$) δ 9.80 (broad s, 1H), 4.62 (m, 2H), 4.20 (m, 1H), 3.85–3.60 (m, 3H), 3.40 (m, 3H), 2.80 (m, 1H), 2.45 –2.05 (m, 4H), 1.95–1.10 (broad m, 27H), 0.95 (broad t, 9H), 0.55 (broad q, 6H).

H: (5Z)-(9S, 11R, 15R)-11,15-Bis-(tetrahydropyran-2-yloxy)-15-cyclohexyl-2,3,4,16,17,18,19,20-octanor-9-(triethylsilyloxy)-5-prostenoic Acid Methyl Ester (12):

A solution of 18-crown-6 (8.50 g, 32.1 mmol) and bis(2,2,2-trifluoroethyl) (methoxycarbonylmethyl)phosphonate (3.72 g, 11.7 mmol) in 110 mL of THF was cooled to −78° C. Potassium bis(trimethylsilyl) amide (KHMDS) (0.5M in toluene, 23.4 mL, 11.7 mmol) was added to the above mixture and the solution was stirred for 15 min. Aldehyde 11 (6.11 g, 10.7 mmol) in 5.0 mL of THF was added dropwise over a period of 15 min. The reaction was stirred at −78° C. for 2 h, then warmed up to 0° C. and stirred at that temperature for 2 more hours. The reaction was quenched by adding 50 mL of saturated aqueous NH$_4$Cl and the mixture was allowed to warm to room temperature. Layers were separated and the aqueous layer was extracted with 2×50 mL of EtOAc. Combined organic layers were washed with 2×50 mL of brine and dried (K$_2$CO$_3$). Filtration and solvent removal gave a crude yellow oil which was purified by passage through a short plug of silica to afford a mixture of 12 and its E isomer (9:1 ratio, 6.28 g, 95% yield). Isomers were separated by chromatography on silica gel (R$_f$=0.56, and 0.47, for the major and minor isomers respectively, 40% Et$_2$O/hexane); 4.57 g of pure 12 and 0.97 g of a 1:1 E/Z mixture were isolated. $^1$H NMR (CDCl$_3$) δ 6.35 (m, 1H), 5.78 (broad d, J=12.0 Hz, 1H), 4.65 (m, 2H), 4.28 (m, 1H), 3.90 (m, 2H), 3.70 (s, 3H), 3.55–3.30 (m, 3H), 2.80 (m, 2H), 2.35–2.05 (m, 1H), 2.00–1.10 (broad m, 30H), 0.95 (broad t, 9H), 0.60 (broad q, 6H).

I: (5Z)-(9S, 11R, 15R)-11,15-Bis-(tetrahydropyran-2-yloxy)-15-cyclohexyl-2,3,4,16,17,18,19,20-octanor-9-(triethylsilyloxy)-5-prosten-1-ol (13):

A solution of 12 (2.0 g, 3.22 mmol) in 20 mL of anhydrous THF was cooled to 0° C. under N$_2$. A solution of diisobutylaluminum hydride (1.5M in toluene, 6.5 mL, 9.66 mmol) was added dropwise and the resulting mixture was stirred at 0° C. for 2 h. The reaction was then quenched by careful addition of CH$_3$OH (5 mL), allowed to warm up to ambient temperature, and diluted with 50 mL of THF. The resulting cloudy solution was treated with 50 mL of a saturated aqueous solution of sodium potassium tartrate and the biphasic mixture was stirred for 1 h. Layers were then separated and the aqueous layer was extracted with 2×50 mL of THF. Organic extracts were combined, washed with brine (50 mL), and dried (MgSO$_4$). Filtration and solvent removal gave a pale yellow oil which was purified by chromatography on silica gel (R$_f$=0.26, 4:6 Et$_2$O/hexane) to yield 13 (1.95 g, 95% yield) as a colorless oil. This compound was used immediately in the subsequent reaction. $^1$H NMR (CDCl$_3$) δ 5.65 (m, 2H), 4.65 (m, 2H), 4.30–3.25 (broad m, 5H), 2.40–2.05 (broad m, 4H), 2.00–1.10 (broad m, 32H), 1.00 (broad t, 9H), 0.60 (broad q, 6H).

J: (5Z)-(9S, 11R, 15R)-11,15-Bis-(tetrahydropyran-2-yloxy)-15-cyclohexyl-9-hydroxy-3-oxa-16,17,18,19,20-pentanor-5-prostenoic Acid t-Butyl Ester (15):

A mixture of 13 (1.95 g, 3.28 mmol), t-butyl bromoacetate (5.11 g, 26.24 mmol), tetrabutylammonium hydrogen sulfate (0.8 g, 2.35 mmol), toluene (45 mL) and 25% (w/w) aqueous NaOH (30 mL) was stirred vigorously at room temperature for 18 h. Layers were separated and the aqueous layer was extracted with 2×25 mL of EtOAc. Combined organic extracts were washed with brine (15 mL), dried (MgSO$_4$, and concentrated. Crude product was purified by chromatography on silica gel (R$_f$=0.56, 20% EtOAc/hexane) to yield 2.19 g of 14 (contaminated with some t-butyl bromoacetate) and 0.48 g of the starting allyl alcohol 13. The allyl ether 14 thus obtained was used in the desilylation reaction without further purification.

The silyl ether 14 (0.5 g) obtained above was dissolved in 3.0 mL of DMSO and to it was added 2.2 mL of tetrabutylammonium fluoride (1.0M in THF, 2.2 mmol). The mixture was stirred at ambient temperature for 30 min and then partitioned between 50 mL EtOAc and 10 mL brine. The aqueous layer was extracted with 2×10 mL of EtOAc and the combined organic extracts were dried over MgSO$_4$. Evaporation and chromatography on silica gel (R$_f$=0.44, 50% EtOAc/hexane) afforded 0.28 g of 15 as a colorless oil. $^1$H NMR (CDCl$_3$) δ 5.65 (m, 2H), 4.62 (m, 2H), 4.16 (m,. 1H), 4.10–3.75 (m, 3H), 3.95 (s, 2H), 3.45 (m, 2H), 2.50–0.90 (broad m, 35H), 1.46 (s, 9H); High Resolution CI MS m/z (CI) calcd for C$_{34}$H$_{59}$O$_8$ (MH$^+$) 595.4209, found 595.4208.

K: (5Z)-(9R, 11R, 15R)-9-Chloro-15-cyclohexyl-11,15-dihydroxy-3-oxa-16,17,18,19,20-pentanor-5-prostenoic Acid t-Butyl Ester (17):

The hydroxyester 15 (0.28 g, 0.47 mmol) was dissolved in 4.0 mL of a stock solution containing 48.0 mL of CH$_3$CN, 0.79 mL of pyridine, and 0.97 mL of CCl$_4$. Triphenylphosphine (0.18 g, 0.70 mmol) was added and the resulting mixture was stirred at ambient temperature for 17 h. The reaction mixture was treated with 10 mL of a 1:1 solution of Et$_2$O/hexanes and the precipitate formed was filtered off. The filtrate was concentrated and purified by chromatography (silica gel, R$_f$=0.47, 40:60 Et$_2$O / hexanes) to yield pure 16 (90 mg, 34%) as a colorless oil.

A solution of 16 (80 mg, 0.13 mmol) in 7.0 mL of 65% (v/v) aqueous acetic acid was heated to 65°–70° C. for 45 min. The reaction mixture was cooled to room temperature and concentrated. The resulting residue was redissolved in anhydrous ETOH and the solvent was again evaporated. The residue thus obtained was purified by chromatography on silica gel (R$_f$=0.4, 60:40 EtOAc/hexanes) to yield 60 mg (100%) of 17 as a colorless, viscous oil. $^1$H NMR (CDCl$_3$) δ 5.69 (m, 2H), 4.32–3.85 (m, 5H), 3.38 (m, 1H), 2.50–1.95 (m, 5H), 1.95–0.80 (broad m, 29H) 1.43 (s, 9H); $^{13}$C NMR (CDCl$_3$) δ 169.9, 131.7, 126.8, 82.0, 75.6, 75.1, 67.9, 66.6, 54.2, 51.0, 44.3, 43.7, 31.4, 30.3, 30.1, 29.3, 28.1, 28.0, 26.5, 26.3, 26.1; High Resolution Cl MS m/z calcd for C$_{24}$H$_{42}$O$_5$Cl (MH$^+$) 445.2720, found 445.2716.

L: (5Z)-(9R, 11R, 15R)-11-(t-Butyldimethylsiloxy)-9-chloro-15-cyclohexyl-15-hydroxy-3-oxa-16,17,18,19,20-pentanor-5-prostenoic acid t-butyl ester (18):

To a mixture of 127 mg (0.285 mmol) of diol 17, 49 mg (0.72 mmol) of imidazole, 10 mg (0.082 mmol) of 4-(dimethylamino)pyridine (DMAP), and 5 mL of CH$_2$Cl$_2$ was added 90 mg (0.59 mmol) of tert-butyldimethylsilyl chloride. After stirring overnight, 10 mL of saturated NH$_4$Cl was added, the mixture was extracted with CH$_2$Cl$_2$ (3×10 mL), the combined organic layers were dried over MgSO$_4$, filtered and concentrated, and the residue was chromatographed on silica gel (20% ethyl acetate in hexane) to afford 87 mg (55%) of 18.

M: (5Z)-(9R, 11R, 15R)-11-(t-Butyldimethylsiloxy)-9-chloro-15-cyclohexyl-15-methoxy-3-oxa-16,17,18,19,20-pentanor-5-prostenoic acid t-butyl ester (19):

A mixture of 80 mg (0.14 mmol) of 18, 100 mg (0.52 mmol) of 2,6-di-t-butylpyridine, 80 mg (0.51 mmol) of methyl trifluoromethanesulfonate, and 2 mL of CH$_2$Cl$_2$ was refluxed overnight. The reaction was cooled to room temperature, poured into 10 mL of saturated NaHCO$_3$, extracted with CH$_2$Cl$_2$ (3×10 mL), the combined organic layers were dried over MgSO$_4$ filtered, and concentrated, and the residue was chromatographed on silica gel (10% ethyl acetate in hexane) to afford 35 mg (44%) of 19.

N: (5Z)-(9R, 11R, 15R)-9-Chloro-15-cyclohexyl-11-hydroxy-15-methoxy-3-oxa-16,17,18,19,20-pentanor-5-prostenoic acid t-butyl ester (II):

To a mixture of 32 mg (0.056 mmol) of 19 and 1.5 mL of THF was added 0.12 mL (0.12 mmol) of 1M tetrabutylammonium fluoride (TBAF) in THF. After 30 min, 4 mL of saturated NH$_4$Cl was added, the mixture was extracted with ethyl acetate (3×5 mL), the combined organic layers were dried over MgSO$_4$, filtered, and concentrated, and the residue was chromatographed on silica gel (40% ethyl acetate in hexane) to afford 24 mg (93%) of II. $^{13}$C NMR (CDCl$_3$) δ 169.77 (C), 130.90 (CH), 127.43 (CH), 85.89 (CH), 81.69 (C), 76.05 (CH), 67.83 (CH), 66.56 (CH$_2$), 61.00 (CH), 57.83 (CH$_3$), 54.06 (CH), 51.92 (CH), 44.45 (CH$_2$), 40.65 (CH), 29.92 (CH$_2$), 29.83 (CH$_2$), 29.02 (CH$_2$), 28.42 (CH$_3$), 28.10 (CH$_2$), 26.64 (CH$_2$), 26.37 (CH$_2$). CI MS, m/z calcd. for C$_{25}$H$_{44}$O$_5$Cl (MH$^+$) 459.2877, found 459.2877.

EXAMPLE 2

SYNTHESIS OF COMPOUND III

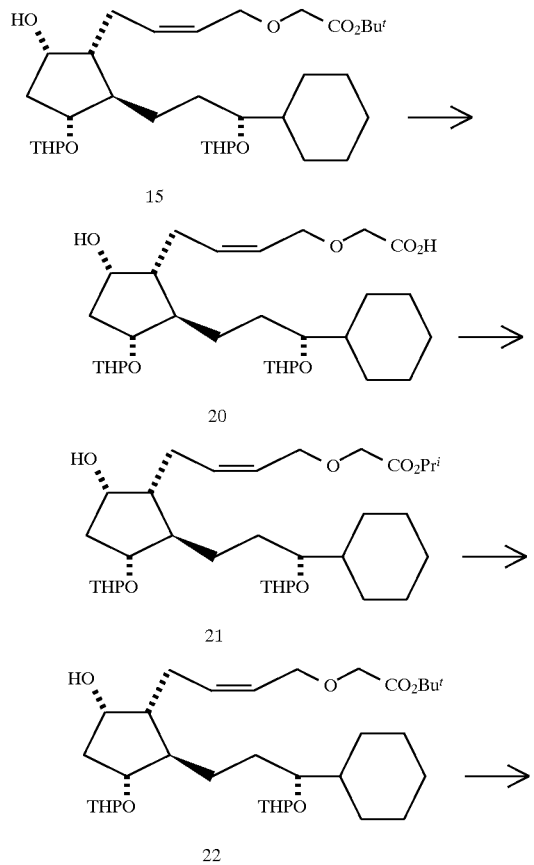

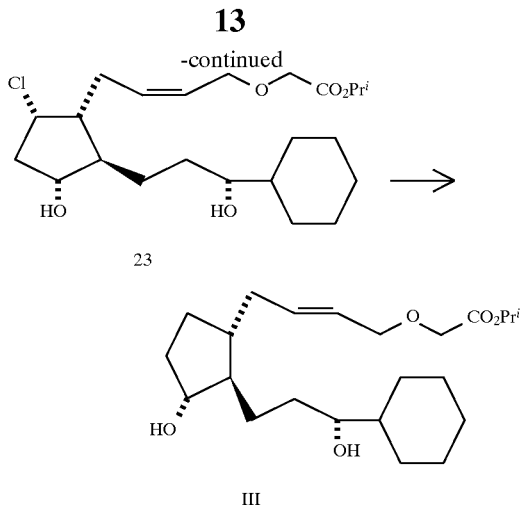

A: (5Z)-(9S, 11R, 15R)-11,15Bis-(tetrahydropyran-2-yloxy)-15-cyclohexyl-9-hydroxy-3oxa-16,17,18,19,20-pentanor-5-prostenoic Acid (20):

Hydroxyester 15 (0.454 g; 0.76 mmol; see Example 1) was dissolved in 10 mL of methanol and 2 mL of water. Lithium hydroxide monohydrate (0.16 g; 500 mol %) was added and the mixture was stirred at room temperature. After 18 h, 20 mL of saturated, aqueous $KH_2PO_4$ and 20 mL $CH_2Cl_2$ were added, layers were separated, and the aqueous phase was washed with additional $CH_2Cl_2$ (3×20 mL). Combined organic layers were dried over $Na_2SO_4$, filtered, and concentrated, affording 0.47 g of a colorless oil which was used directly in the next reaction.

B: (5Z)-(9S, 11R 15R)-11,15-Bis-(tetrahydropyran-2-yloxy)-1-cyclohexyl-9-hydroxy-3-oxa-16,17,18,19,20-pentanor-5-prostenoic Acid Isopropyl Ester (21):

Crude acid 20 from above (0.23 g; 0.43 mmol) was dissolved in 10 mL of acetone. DBU (0.25 mL; 400 mol %) and isopropyl iodide (0.21 g; 300 mol %) were added and the mixture was stirred for 12 h at room temperature. After evaporation, the residue was applied to a silica gel column and eluted with hexane/EtOAc, 1/1, to afford 0.157 g (63%) of isopropyl ester 21 as a colorless oil. $R_f$=0.49; $^1$H NMR (CDCl) δ (characteristic peaks only) 5.80–5.52 (m, 2H), 5.15 (sep, 1H, J=6.2 Hz), 4.03 (broad s, 2H), 1.27 (d, 6H, J=6.2 Hz).

C: (5Z)-(9R, 11R, 15R)-9Chloro-15-cyclohexyl-11,15-dihydroxy-3-oxa-16,17,18,19,20-pentanor-5-prostenoic Acid Isopropyl Ester (23):

The hydroxyester 21 (0.146 g; 0.25 mmol) was dissolved in 3.0 mL of a stock solution containing 48 mL of $CH_3CN$, 0.79 mL of pyridine, and 0.97 mL of $CCl_4$. Triphenylphosphine (0.10 g; 150 mol %) was added and the resulting mixture was stirred at room temperature for 17 h. The reaction mixture was treated with 10 mL of a 1:1 solution of $Et_2O$/hexanes and the precipitate was filtered off. The filtrate was concentrated and chromatographed on silica gel (hexane/EtOAc, 4/1), affording 0.108 g of a colorless oil which consisted of a nearly equimolar mixture of desired chlorinated material 22 with its undesired 5,8-diene elimination product.

A solution of crude 22 from above in 10 mL of 65% (v/v) aqueous acetic acid was warmed to 65° C. for 45 min. The mixture was then cooled to room temperature and concentrated. The resulting residue was then purified by silica gel chromatography (hexane/EtOAc, 2/3), affording 27 mg (25% based on 21) of pure 23 ($R_f$=0.56) as a colorless oil with 69 mg of a mixture of 23 and its 5,8-diene elimination product ($R_f$=0.45). $^1$H NMR (CDCl) δ 5.67 (m, 2H), 5.08 (septet, 1H, J=6.1), 4.30–3.95 (m, 6H), 3.40 (m, 1H), 2.35 (m, 2H), 2.30–2.00 (m, 3H), 1.93–1.35 (m, 12H), 1.25 (d, 6H, J=6.2 Hz), 1.22–0.90 (m, 6H); $^{13}$C NMR (CDCl$_3$) δ 170.2, 131.8, 126.7, 75.7, 75.2, 68.8, 67.6, 66.7, 61.2, 54.2, 51.1, 44.4, 43.6, 31.4, 30.2, 30.1, 29.3, 28.0, 26.5, 26.3, 26.1, 21.8; High Resolution CI MS m/z calcd for $C_{23}H_{40}O_5Cl$ ($MH^+$) 431.2564, found 431.2569.

D: (5E)-(11R, 15R)-15-Cyclohexyl-11,15-dihydroxy-3-oxa-16,17,18,19,20-pentanor-5-prostenoic acid isopropyl ester (III):

To a solution of the ester 23 (390 mg, 0.90 mmol) and AIBN (10 mg) in anhydrous toluene (9.0 mL) was added $nBu_3SnH$ (0.47 mL, 1.80 mmol). The resulting mixture was heated at reflux for 4h. The solvent was evaporated and the residue was applied to a silica gel column for purification. The product III ($R_f$=0.4, 60% EtOAc/hexane) was isolated as a colorless oil (340 mg isolated, 95% yield). $^1$H NMR (CDCl$_3$) δ 5.60 (m, 2H), 5.05 (septet, J=6.5 Hz, 1H), 3.98 (m, 4H), 3.85 (m, 1H), 3.30 (m, 1H), 2.22 (m, 1H), 2.00 (m, 1H), 1.80–0.85 (broad m, 23H), 1.21 (d, J=6.4 Hz, 6H); $^{13}$C NMR (CDCl$_3$) δ 170.11, 134.59, 126.54, 79.15, 76.35, 72.07, 68.50, 67.18, 53.57, 44.21, 43.62, 38.21, 34.19, 32.05, 29.47, 29.32, 28.94, 27.98, 26.56, 26.36, 26.21, 21.84.

EXAMPLE 3

SYNTHESIS OF COMPOUND IV

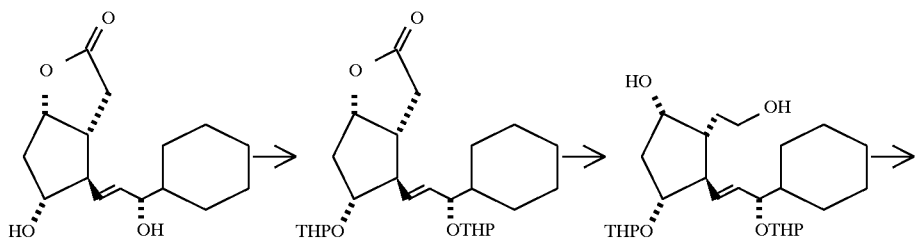

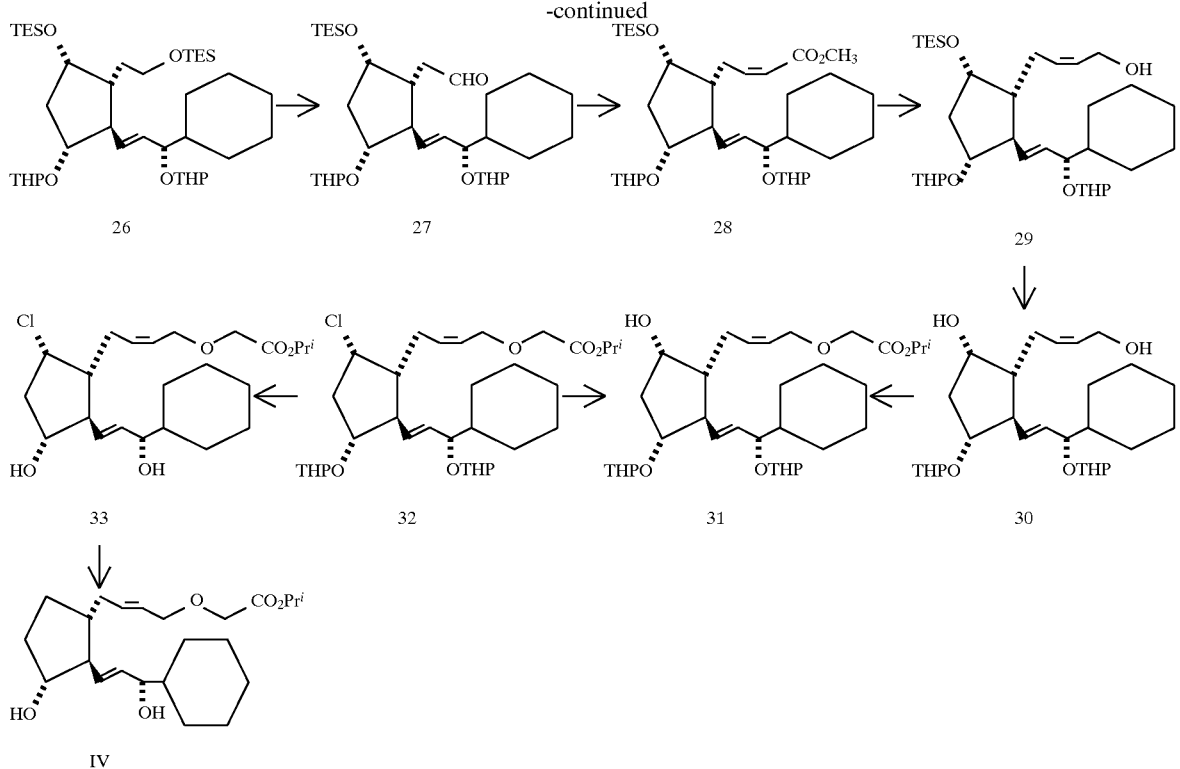

A: (3aR, 4R, 5R, 6aS)-4-[(E)-(3S)-3-Cyclohexyl-3-(tetrahydropyran-2-yloxy)propenyl]-hexahydro-5-(tetrahydropyran-2-yloxy)-2H-cyclopenta[b]furan-2-one (24):

To 15.7 g (55.9 mmol) of diol 6 in 120 mL of $CH_2Cl_2$ at 0° C. was added 12.0 g (142 mmol) of 3,4-dihydro-2H-pyran (DHP) and 520 mg (2.7 mmol) of p-toluenesulfonic acid monohydrate (pTSA). After 1 h at 0° C., 100 mL of saturated $NaHCO_3$ was added, the mixture was extracted with $CH_2Cl_2$ (3×100 mL), the combined organic layers were dried over $MgSO_4$ filtered and concentrated and the residue was chromatographed on silica gel (40% ethyl acetate in hexane) to afford 13.3 g (53%) of bis-THP ether 24.

B: (13E)-(9S,11R,15S)-11,15-Bis(tetrahydropyran-2-yloxy)-15-cyclohexyl-2,3,4,5,6,16,17,18,19,20-decanor-9-hydroxy-13-prostenol (25):

To a solution of 15.0 g (33.4 mmol) of 24 in 150 mL of THF at 0° C. was added 53 mL (80 mmol) of 1.5M solution of diisobutylaluminum hydride (DIBAL-H) in toluene. After 3h the reaction was poured into 300 mL of 1:1 ethyl acetate:saturated sodium potassium tartrate and stirred for 1 h. The layers were separated, the aqueous layer was extracted with ethyl acetate (3×100 mL), the combined organic layers were dried over $MgSO_4$, filtered and concentrated to afford 14.89 g (98%) of crude diol 25.

C: (13E)-(9S,11R,15S)-11,15-Bis(tetrahydropyran-2-yloxy)-15-cyclohexyl-2,3,4,5,6,16,17,18,19,20-decanor-9-(triethlsiloxy)-13-prostenol triethylsilyl ether (26):

To a mixture of 14.8 g (32.7 mmol) of 22, 5.94 g (87.4 mmol) of imidazole, 0.44 g (3.6 mmol) of DMAP, and 150 mL of $CH_2Cl_2$ was added 11.5 g (76.3 mmol) of triethylsilyl chloride. After 5 h, 150 mL of saturated $NH_4Cl$ was added, the layers were separated, and the aqueous layer was extracted with $CH_2Cl_2$ (2×100 mL). The combined organic layers were dried over $MgSO_4$, filtered, and concentrated, and the residue was chromatographed on silica gel (10% ethyl acetate in hexane) to afford 21.9 g (100%) of bis-silyl ether 26.

D: (13E)-(9S,11R,15S)-11,15-Bis(tetrahydropyran-2-yloxy)-15-cyclohexyl-2,3,4,5,6,16,17,18,19,20-decanor-9-(triethylsiloxy)-13-prostenal (27):

To 12.5 g (98.6 mmol) of oxalyl chloride in 150 mL of $CH_2Cl_2$ at −78° C. was added dropwise a solution of DMSO (13.0 g, 166 mmol) in 15 mL of $CH_2Cl_2$. After 30 min, a solution of 26 (22.4 g, 32.9 mmol) in 60 mL of $CH_2Cl_2$. After 30 min, a solution of 26 (22.4 g, 32.9 mmol) in 60 mL of $CH_2Cl_2$ was added dropwise. After 5 h, 36 g (360 mmol) of $NEt_3$ was added, and the reaction was stirred for 30 min at −78° C. and then at room temperature for 30 min. The mixture was poured into 200 mL of saturated $NH_4Cl$ and extracted with $CH_2Cl_2$ (3×150 mL), the combined organic layers were dried over $MgSO_4$, filtered, and concentrated, and the residue was chromatographed on silica gel (20% ethyl acetate in hexane) to afford 18.3 g (99%) of aldehyde 27.

E: (5Z, 13E)-(9S,11R, 15S)-11,15-Bis(tetrahydropyran-2-yloxy)-15-cyclohexyl-2,3,4,16,17,18,19,20octanor-9-(triethylsiloxy)-5,13-prostadienoic acid methyl ester (28):

To a mixture of 16.5 g (51.9 mmol) of bis(2,2,2-trifluoroethyl) (methoxycarbonylmethyl)phosphonate, 28.2 g (107 mmol) of 18-crown-6, and 200 mL of THF at −78° C. was added dropwise 85 mL (42.5 mmol) of 0.5M KHMDS in toluene. After 30 min, a solution of 18.3 g (32.4 mmol) of 27 in 50 mL of THF was added dropwise and the reaction stirred for 2 h. The mixture was poured into 150 mL of saturated $NH_4Cl$, extracted with ethyl acetate (3×100 mL), the combined organic layers were dried over $MgSO_4$, filtered and concentrated, and the residue was chromatographed on silica gel (15% ethyl acetate in hexane) to afford 9.78 g (49%) of crotonate 28, as well as 3.58 g (18%) of a mixture of olefin cis:trans isomers.

F: (5Z, 13E)-(9S,11R, 15S)-11,15-Bis(tetrahydropyran-2-yloxy)-15-cyclohexyl-2,3,4,16,17,18,19,20-octanor-9-(triethylsiloxy)-5,13-prostadienol (29):

To a solution of 9.11 g (14.7 mmol) of 28 in 40 mL of THF at 0° C. was added dropwise 24 mL (36 mmol) of a 1.5M solution of DIBAL-H in toluene. After 1 h, the reaction was added to 100 mL of saturated NH$_4$Cl, extracted with ethyl acetate (3×75 mL), the combined organic layers were dried over MgSO$_4$, filtered, and concentrated to afford 8.7 g (100%) of crude allyl alcohol 29.

G: (5Z, 13E)-(9S,11R, 15S)-11,15-Bis(tetrahydropyran-2-yloxy)-15-cyclohexyl-9-hydroxy-2,3,4,16,17,18,19,20-octanor-5,13-prostadienol (30):

To a solution of 8.7 g (14.7 mmol) of 29 in 60 mL of THF at 0° C. was added 20 mL (20 mmol) of a 1M solution of TBAF in THF. After 1 h, 75 mL of saturated NH$_4$Cl was added, the mixture was extracted with ethyl acetate (3×75 mL), the combined organic layers were dried over MgSO$_4$, filtered, and concentrated, and the residue was chromatographed on silica gel (3/2 ethyl acetate/hexane) to afford 3.79 g (54%) of diol 30.

H: (5Z, 13E)-(9S,11R, 15S)-11,15-Bis(tetrahydropyran-2-yloxy)-15-cyclohexyl-9-hydroxy-3-oxa-16,17,18,19,20-pentanor-5,13-prostadienoic acid isopropyl ester (31):

A mixture of 30 (3.76 g, 7.7 mmol), NaOH (6.1 g, 150 mmol), water (30 mL), toluene (30 mL), tetrabutylammonium hydrogen sulfate (1.05 g, 3.1 mmol), and isopropyl bromoacetate (3.63 g, 20.1 mmol) at room temperature was vigorously stirred for 30 min. The layers were separated, the aqueous layer was extracted with ethyl acetate (2×30 mL), the combined organic layers were dried over MgSO$_4$, filtered and concentrated, and the residue was chromatographed on silica gel (40% ethyl acetate in hexane) to afford ester 31 (3.06 g, 69%).

I: (5Z, 13E)-(9R,11R, 15S)-11,15-Bis(tetrahydropyran-2-yloxy)-9 chloro-15-cyclohexyl-3-oxa-16,17,18,19,20-pentanor-5,13-prostadienoic acid isopropyl ester (32):

To a mixture of 31 (3.0 g, 5.2 mmol) and 30 mL of pyridine at 0° C. was added methanesulfonyl chloride (1.48 g, 12.9 mmol). The reaction was brought to room temperature after 15 min, stirred for an additional 1.5 h, and poured into a suspension of Bu$_4$NCl (14.5 g, 52.2 mmol) in 45 mL of toluene. The mixture was stirred at room temperature overnight, at 55°–60° C. for 2 h, poured into 100 mL of saturated NH$_4$Cl, extracted with ethyl acetate (3×75 mL), the combined organic layers were dried over MgSO$_4$, filtered, and concentrated, and the residue was chromatographed on silica gel (30% ethyl acetate in hexane) to afford 3.0 g of an oil which consisted of a mixture of chlorinated compound 32 and the 8,9-olefin elimination by-product. This mixture was used in the next step without further purification.

T: (5Z, 13E)-(9R,11R, 15S)-9-Chloro-15-cyclohexyl-11,15dihydroxy-3-oxa-16,17,18,19,20-pentanor-5,13prostadienoic acid isopropyl ester (33):

The sample from above (3.0 g) was dissolved in 40 mL of isopropyl alcohol and 5 mL of water was added, followed by 2.3 mL of 12M HCl. After 3 h, saturated NaHCO$_3$ was added (50 mL), the mixture was extracted with ethyl acetate (3×50 mL), the combined organic layers were dried over MgSO$_4$, filtered, and concentrated, and the residue was purified by radial chromatography (20/1 toluene/isopropanol) to afford 324 mg of pure chloride 33 (32%), as well as 278 mg (28%, calculated as the chloride) of a mixture of 33 with the 8,9-olefin. $^{13}$C NMR (CDCl) δ 170.04 (C), 134.51 (CH), 132.64 (CH), 130.43 (CH), 127.58 (CH), 77.34 (CH), 75.40 (CH), 68.60 (CH), 67.60 (CH$_2$), 66.64 (CH$_2$), 59.64 (CH), 55.95 (CH), 53.36 (CH), 43.61 (CH), 43.57 (CH$_2$), 28.83 (CH$_2$), 28.70 (CH$_2$), 26.49 (CH$_2$), 26.06 (CH$_2$), 25.99 (CH$_2$), 21.82 (CH). CI MS, m/z calcd. for C$_{23}$H$_{38}$O$_5$Cl (MH$^+$) 429.2408, found 429.2408.

K: (5E, 13E)-(9R,11R, 15S)-1-cyclohexyl-11,15-dihydroxy-3-oxa-16,17,18,19,20-pentanor-5,13-prostadienoic acid isopropyl ester (IV):

A mixture of 33 (60 mg, 0.14 mmol), benzene (3 mL), AIBN (10 mg), and Bu$_3$SnH (90 mg, 0.31 mmol) was deoxygenated by purging with N$_2$ for 15 min, and was heated at reflux for 1 h. The reaction was concentrated and chromatographed on silica gel (3:2 ethyl acetate:hexane) to afford 43 mg (78%) of dechlorinated product IV. $^{13}$C NMR (CDCl$_3$) δ 169.98 (C), 134.27 (CH), 134.22 (CH), 133.94 (CH), 126.62 (CH), 77.76 (CH), 77.72 (CH), 71.92 (CH$_2$), 68.41 (CH), 67.06 (CH$_2$), 58.01 (CH), 43.33 (CH), 42.18 (CH), 36.99 (CH$_2$), 32.02 (CH$_2$), 28.94 (CH$_2$), 28.72 (CH$_2$); 27.38 (CH$_2$), 26.48 (CH$_2$), 26.03 (CH), 25.96 (CH$_2$), 21.74 (CH$_3$). CI MS, m/z calcd. for CH$_{23}$H$_{39}$O$_5$ (MH$^+$) 395.2798, found 395.2798.

EXAMPLE 4

SYNTHESIS OF COMPOUND V

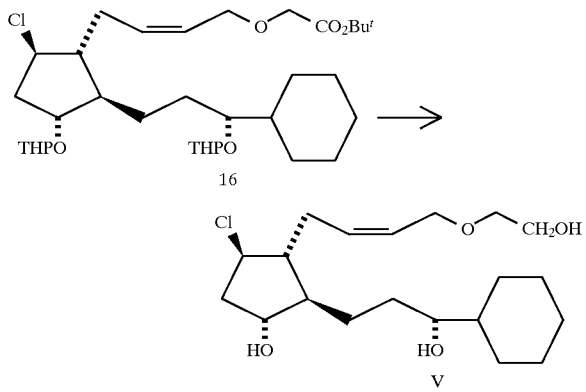

(5Z)-(9R,11R, 15R)-9-Chloro-15-cyclohexyl-11,15-dihydroxy-3-oxa-16,17,18,19,20-pentanor-5-prostenol (V):

A solution of the ester 16 (150 mg, 0.24 mmol) in THF (5.0 mL) was cooled to 0° C. and to it DIBAL-H (1.5M in toluene, 0.5 mL, 0.72 mmol) was added and the resulting mixture was stirred at 0° C. for 2.5 h. The reaction was carefully quenched with a saturated solution of potassium sodium tartrate (10 mL) and the biphasic mixture was stirred at ambient temperature for 1 h. The organic layer was then separated and the aqueous layer was extracted with EtOAc (5×10 mL). The combined organic layers were dried (Na$_2$SO$_4$), filtered, and concentrated to afford a pale yellow liquid which was purified by chromatography on silica gel. The intermediate alcohol (R$_f$=0.15, 30% EtOAc/hexanes) was isolated (114 mg, 87% yield) as a colorless oil and was used in the subsequent reaction.

The above alcohol (54 mg, 0.09 mmol) was mixed with 65% acetic acid/water (15 mL) and the result was heated at 70° C. for 1 h. The solvent was evaporated and the crude was applied to a column of silica gel for purification. The triol V (R$_f$=0.15 EtOAc) was isolated as a colorless oil (33 mg, 88% yield). $^1$H NMR (CDCl$_3$) δ 5.68 (m, 2H), 4.08 (m, 4H), 3.74 (m, 2H), 3.57 (m, 2H), 3.42 (m, 1H), 2.37 (m, 2H), 2.35–1.90 (m, 4H), 1.85–0.90 (broad m, 18H); $^{13}$C NMR (CDCl$_3$) δ 131.06, 127.52, 75.80, 75.54, 71.94, 66.38, 61.82, 60.82, 54.05, 50.87, 44.69, 43.60, 31.29, 29.71, 29.46, 29.22, 28.08, 26.48, 26.28, 26.14; CI MS calcd. for C$_{20}$H$_{36}$O$_4$Cl (MH$^+$) 375.2302, found 375.2299.

EXAMPLE 5

SYNTHESIS OF COMPOUND VI

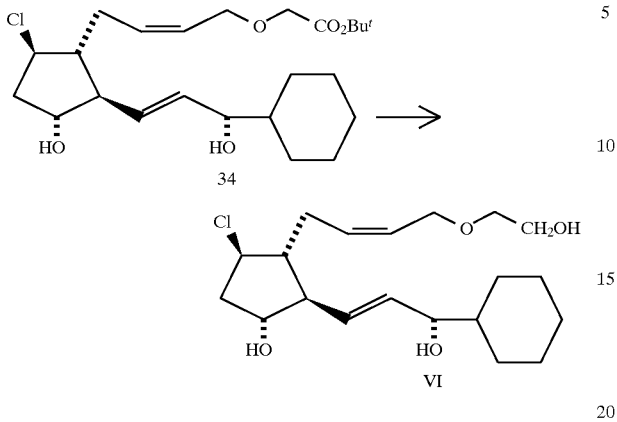

(5Z)-(9R,11R, 15S)-9-Chloro-15-cyclohexyl-11,15-dihydroxy-3-oxa-16,17,18,19,20-pentanor-5,13prostadienol (VI):

To a solution of ester 34 (41 mg, 0.093 mmol) (German patent DE 3724189) in 5 mL of THF at 0° C. was added a 1.5M solution of DIBAL-H (0.7 mL, 1.05 mmol). After warming to room temperature and stirring for 1.5h, 15 mL of saturated $NH_4Cl$ was added, the mixture was extracted with ethyl acetate (3×15 mL), the combined organic layers were dried over $MgSO_4$, filtered, and concentrated, and the residue was chromatographed on silica gel (ethyl acetate) to afford triol VI (21 mg, 68%). $^{13}C$ NMR ($CDCl_3$) δ 134.59 (CH), 133.00 (CH), 129.61 (CH), 128.21 (CH), 77.56 (CH), 75.16 (CH), 71.54 ($CH_2$), 67.93 ($CH_2$), 66.46 ($CH_2$), 61.76 ($CH_2$), 59.49 ($CH_2$), 55.85 ($CH_2$), 53.23 (CH), 43.43 ($CH_2$), 28.81 ($CH_2$), 28.56 ($CH_2$), 26.46 ($CH_2$), 26.02 ($CH_2$), 26.94 (CH), 25.57 ($CH_2$). CI MS, m/z calcd. for $C_{20}H_{34}O_4Cl$ ($MH^+$) 373.2146, found 373.2101.

EXAMPLE 6

SYNTHESIS OF COMPOUND VII

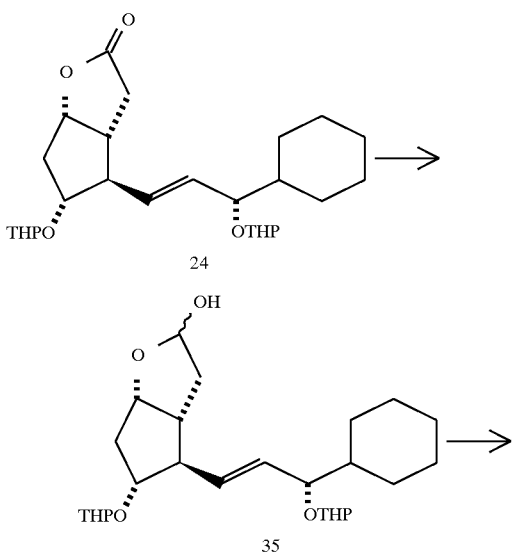

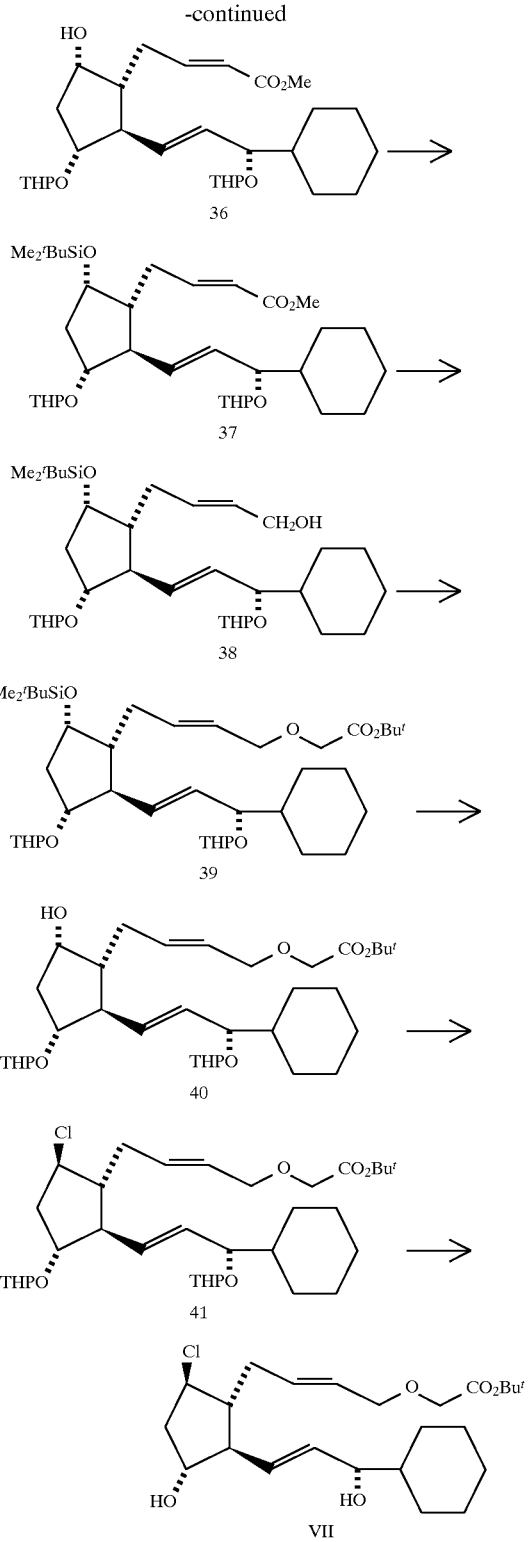

A: (3aR, 4R, 5R, 6aS)-4-[(E)-(3S)-3-Cyclohexyl-3-(tetrahydropyran-2-yloxy)propenyl]-hexahydro-5-(tetrahydropyran-2-yloxy)-2H-cyclopenta[b]furan-2-ol (35):

To a solution of lactone 24 (5.7 g, 12.7 mmol) in 40 mL of THF at −78° C. was added dropwise a 1.5M solution of DIBAL-H in toluene (11.5 mL, 17.2 mmol). After 2 h, the reaction was poured into 70 mL of a saturated solution of sodium potassium tartrate and was stirred for 30 min. The mixture was extracted with ethyl acetate (3×50 mL), the combined organic layers were dried over MgSO$_4$, filtered and concentrated, and the residue was chromatographed on silica gel (1/1 hexane/ethyl acetate) to afford 4.7 g (82%) of lactol 35.

B: (5E, 13E)-(9S, 11R, 15S)-11,15-Bis(tetrahydropyran-2-yloxy)-15-cyclohexyl-9-hydroxy-2,3,4,16,17,18,19,20-octanor-5,13-prostadienoic acid methyl ester (36):

A mixture of 35 (5.1 g, 11.3 mmol), Ph$_3$PCH=CO$_2$Me (6.6 g, 19.7 mmol), CH$_2$Cl$_2$ (50 mL), and acetic acid (8 drops) was stirred overnight at room temperature. The mixture was concentrated and chromatographed on silica gel (1/1 hexane/ethyl acetate) to afford 5.7 g (99%) of trans-crotonate 36.

C: (5E, 13E)-(9S, 11R, 15S)-11,15-Bis(tetrahydropyran-2-yloxy)-9-(t-butyldimethylsiloxy)-15-cyclohexyl-2,3,4,16,17,18,19,20-octanor-5,13-prostadienoic acid methyl ester (37):

A mixture of 36 (5.7 g, 11.6 mmol), CH$_2$Cl$_2$ (150 mL), imidazole (1.46 g, 21.5 mmol), DMAP (500 mg, 4.1 mmol), and t-butyldimethylsilyl chloride (2.54 g, 16.9 mmol) was stirred for 1 h, 50 mL of saturated NH$_4$Cl was added, the layers were separated, the aqueous layer was extracted with CH$_2$Cl$_2$ (2×50 mL), the combined organic layers were dried over MgSO$_4$, filtered and concentrated, and the residue was chromatographed on silica gel (20% ethyl acetate in hexane) to afford 37 (6.05 g, 84%).

D: (5E, 13E)-(9S, 11R, 15S)-11,15-Bis(tetrahydropyran-2-yloxy)-9-(t-butyldimethylsiloxy)-15-cyclohexyl-2,3,4,16,17,18,19,20-octanor-5,13-prostadienol (38):

To a solution of 37 (6.0 g, 9.8 mmol) in THF (50 mL) at 0° C. was added dropwise a 1.5M solution of DIBAL-H in toluene (16 mL, 24 mmol). The reaction was brought to room temperature and was stirred for 2 h, 75 mL of a saturated solution of sodium potassium tartrate was added, and the mixture was stirred for 35 min. The layers were separated, the aqueous layer was extracted with ethyl acetate (2×50 mL), the combined organic layers were dried over MgSO$_4$, filtered, and concentrated, and the residue was chromatographed on silica gel (25% ethyl acetate in hexane) to afford 38 (4.28 g, 74%).

E: (5E, 13E)-(9S, 11R, 15S)-11,15-Bis(tetrahydropyran-2-yloxy)-9-(t-butydimethylsiloxy)-15-cyclohexyl-3-oxa-16,17,18,19,20-pentanor-5,13-prostadienoic acid t-butyl ester (39):

A mixture of 38 (2.4 g, 4.1 mmol), water (25 mL), toluene (30 mL), NaOH (3.8 g, 95 mmol), Bu$_4$NHSO$_4$ (300 mg, 0.88 mmol), and t-butyl bromoacetate (5.0 g, 25.6 mmol) was stirred vigorously overnight. The layers were separated, the aqueous layer was extracted with ethyl acetate (2×50 mL), the combined organic layers were dried over MgSO$_4$, filtered and concentrated, and the residue was chromatographed on silica gel (20% ethyl acetate in hexane) to afford 39 (1.48 g, 48%).

F: (5E, 13E)-(9S, 11R, 15S)-11,15-Bis(tetrahydropyran-2-yloxy)-15-cyclohexyl-9-hydroxy-3-oxa-16,17,18,19,20-pentanor-5,13-prostadienoic acid t-butyl ester (40):

A mixture of 39 (1.4 g, 2.0 mmol), THF (20 mL), and a 1M solution of TBAF in THF (6 mL, 6 mmol) was stirred for 2 h, saturated NH$_4$Cl was added (30 mL), the layers were separated, the aqueous layer was extracted with ethyl acetate (2×40 mL), the combined organic layers were dried over MgSO$_4$, filtered, and concentrated, and the residue was chromatographed on silica gel (1/1 hexane/ethyl acetate) to afford 40 (0.45 g, 38%).

G: (5E, 13E)-(9R, 11R, 15S)-11,15-Bis(tetrahydropyran-2-yloxy)-9-chloro-15-cyclohexyl-3-oxa-16,17,18,19,20-pentanor-5,13-prostadienoic acid t-butyl ester (41):

A mixture of 40 (430 mg, 0.72 mmol), PPh$_3$ (350 mg, 1.34 mmol), CH$_3$CN (6 mL), pyridine (112 mg, 1.42 mmol), and CCl$_4$ (240 mg, 1.55 mmol) was stirred overnight. The reaction was concentrated and the residue was chromatographed on silica gel (20% ethyl acetate in hexane) to afford 41 as a mixture with the corresponding 8,9-olefin (362 mg, 82% calculated as the chloride). This mixture was separated in the next step.

H: (5E, 13E)-(9R, 11R, 15S)-9-Chloro-15-cyclohexyl-11,15-dihydroxy-3-oxa-16,17,18,19,20-pentanor-5,13-prostadienoic acid t-butyl ester (VII):

A mixture of 41 (310 mg, 0.51 mmol calculated as the chloride), THF (5 mL), water (1 mL), and acetic acid (9 mL) was heated at 65° C. for 1 h. The reaction was concentrated and the residue was chromatographed on silica gel (4/1 ethyl acetate/hexane) to afford VII as a mixture with the corresponding 8,9-olefin (188 mg, 83% calculated as the chloride). The mixture was separated by reverse-phase HPLC to afford pure VII (58 mg, 26% from alcohol 40). $^{13}$C NMR (CDCl$_3$) δ 169.67 (C), 134.67 (CH), 133.09 (CH), 131.18 (CH), 128.56 (CH), 81.62 (C), 77.31 (CH), 75.04 (CH), 71.63 (CH$_2$), 67.59 (CH$_2$), 59.38 (CH), 56.34 (CH), 53.08 (CH), 43.32 (CH), 43.38 (CH$_2$), 33.88 (CH$_2$), 28.87 (CH), 28.77 (CH$_2$), 28.10 (CH$_3$), 26.48 (CH$_2$), 26.05 (CH$_2$), 25.97 (CH$_2$). CI MS m/z calcd. for C$_{24}$H$_{40}$O$_5$Cl$^{37}$ 445.2535, found 445.2574.

EXAMPLE 7

SYNTHESIS OF COMPOUND VIII

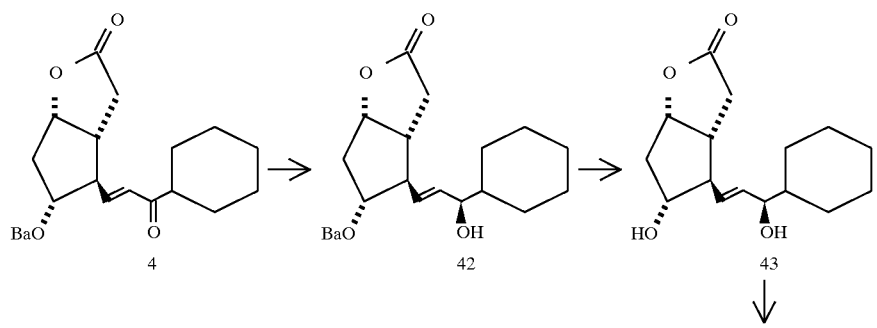

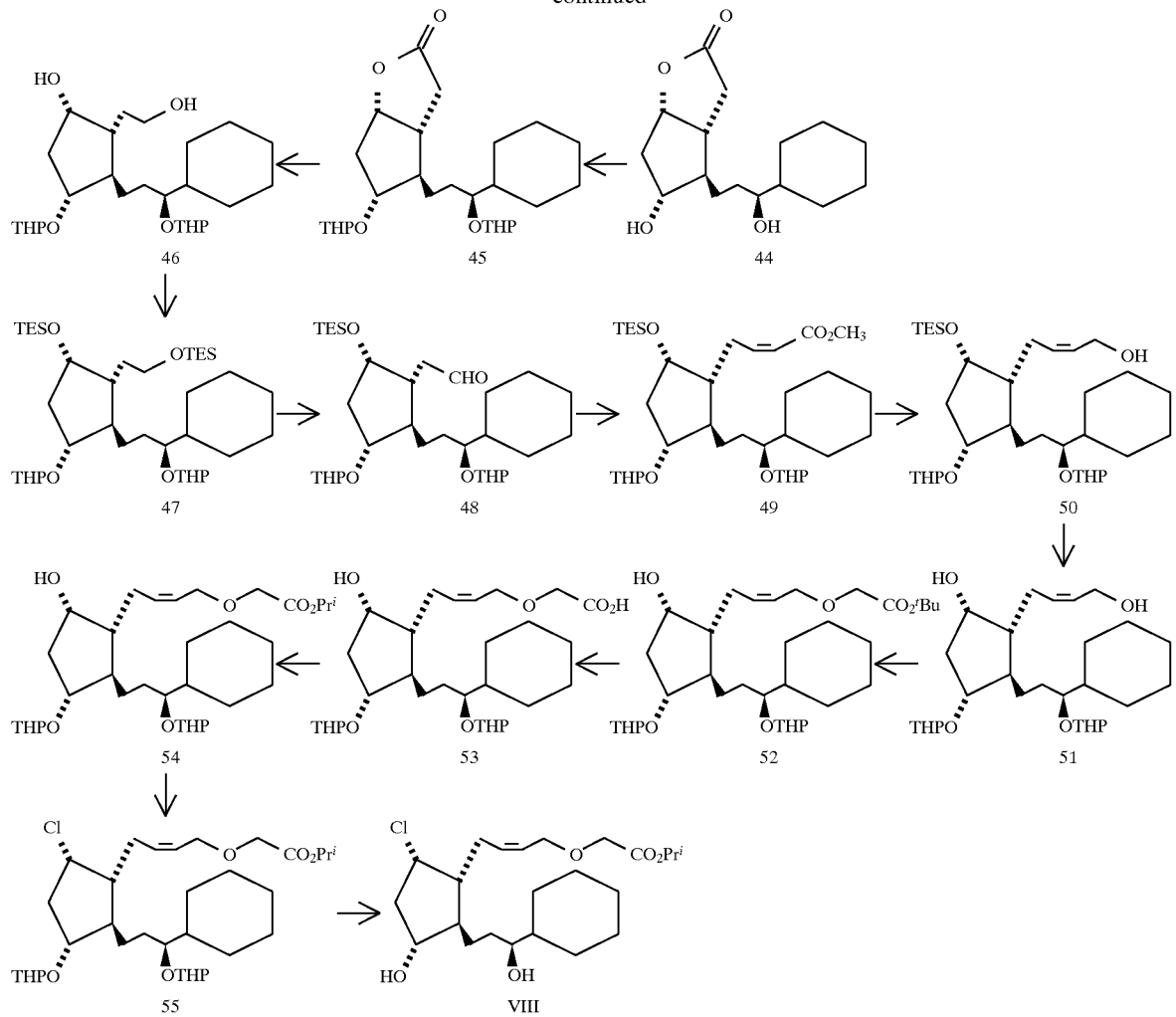

A: 3aR, 4R, 5R, 6aS)-5-(Benzoyloxy)-4-[(E)-(3R)-3-cyclohexyl-3-hydroxy-1-propenyl]-hexahydro-2H-cyclopenta[b]furan-2-one (42):

To a solution of enone 4 (150 g, 392 mmol), cerium trichloride heptahydrate (152 g, 408 mmol), methanol (500 mL), and $CH_2Cl_2$ (1.5 L) at 0° C. was added $NaBH_4$ (14.4 g) in 0.2 g portions over 1 h. After stirring for 2 h, the reaction was poured into 1M HCl (500 mL), the layers were separated, the aqueous layer was extracted with $CH_2Cl_2$ (2×300 mL), and the combined organic layers were dried over $MgSO_4$, filtered, and concentrated to provide 150.4 g (100%) of a 1:1 mixture of the two diastereomeric allylic alcohols. Separation of 200 g of the mixture (from several combined reactions) by HPLC (40% ethyl acetate in hexane) afforded 23.7 g (12%) of alcohol 42.

B: (3aR, 4R, 5R, 6aS)-4-[(E)-(3R)-3-Cyclohexyl-3-hydroxy-propenyl]-hexahydro-5-hydroxy-2H-cyclopenta[b]furan-2-one (43):

To a solution of 42 (7.35 g, 19.1 mmol) in methanol (100 mL) was added $K_2CO_3$ (2.64 g, 19.1 mmol). After 2h, 200 mL of 2M HCl was added, the mixture was extracted with ethyl acetate (3×100 mL), and the combined organic layers were dried over $MgSO_4$, filtered, and concentrated to afford crude diol 43 (5.53 g), which was used in the next step without purification.

C: (3aR, 4R, 5R, 6aS)-4-[(3S)-3-Cyclohexyl-3-hydroxypropyl]-hexahydro-5-hydroxy-2H-cyclopenta[b]furan-2-one (44):

A mixture of 43 (5.3 g, 18.9 mmol), 10% w/w Pd/C (320 mg), ethyl acetate (30 mL), and $CH_2Cl_2$ (10 mL) was hydrogenated in a Parr hydrogenation apparatus for 3 h at 45 psi. The mixture was filtered through Celite and concentrated, and the residue was chromatographed on silica gel (ethyl acetate) to afford 44 (4.3 g, 80%). $^{13}C$ NMR $(CDCl_3)$ δ 177.64 (C), 83.87 (CH), 77.21 (CH), 76.02 (CH), 53.45 (CH), 43.84 (CH), 42.96 (CH), 40.46 ($CH_2$), 35.88 (CH), 31.37 ($CH_2$), 29.23 ($CH_2$), 29.10 ($CH_2$), 27.85 ($CH_2$), 26.41 (CH), 26.22 ($CH_2$), 26.08 ($CH_2$).

D: (3aR, 4R, 5R, 6aS)-4-[(3S)-3-Cyclohexyl-3-(tetrahydropyran-2-yloxy)propyl]-hexahydro-5-(tetrahydropyran-2-yloxy)-2H-cyclopenta[b]furan-2-one (45):

To a mixture of 44 (3.7 g, 12.9 mmol), DHP (2.9 g, 35 mmol), and $CH_2Cl_2$ (80 mL) at 0° C. was added pTSA (300 mg, 1.58 mmol). After 30 min 50 mL of saturated $NaHCO_3$ was added, the layers were separated, the aqueous layer was extracted with $CH_2CL_2$ (2×50 mL), the combined organic layers were dried over $MgSO_4$, filtered, and concentrated, and the residue was chromatographed on silica gel (1/1 hexane/ethyl acetate) to afford bis-THP ether 45 (4.89 g, 89%).

E: (9S, 11R, 15S)-11,15-Bis(tetrahydropyran-2-yloxy)-15-cyclohexyl-2,3,4,6,16,17,18,19,20-decanor-9-hydroxyprostanol (46):

To a suspension of lithium aluminum hydride (920 mg, 24.2 mmol) in 50 mL of THF at 0° C. was added dropwise a solution of lactone 45 (10.87 g, 24.1 mmol) in THF (100 mL). After stirring for 1 h, ethyl acetate was cautiously added dropwise (50 mL), followed by saturated $NH_4Cl$ (100 mL). The mixture was extracted with ethyl acetate (3×100 mL), the combined organic layers were dried over $MgSO_4$, filtered, and concentrated to provide crude diol 46 (9.73 g, 89%), which was used in the next step without purification.

F: (9S, 11R, 15S)-11,15-Bis(tetrahydropyran-2-yloxy)-15-cyclohexyl-2,3,4,5,6,16,17,18,19,20-decanor-9-(triethylsiloxy)prostanol triethylsilyl ether (47):

A mixture of 46 (9.7 g, 21.3 mmol), triethylsilyl chloride (7.36 g, 48.9 mmol), DMAP (289 mg, 2.36 mmol), $NEt_3$ (5.3 g, 52 mmol), and $CH_2Cl_2$ (100 mL) was stirred overnight at room temperature. The mixture was poured into 100 mL of saturated $NH_4Cl$, the layers were separated, the aqueous layer was extracted with $CH_2Cl_2$ (50 mL), the combined organic layers were dried over $MgSO_4$, filtered, and concentrated, and the residue was chromatographed on silica gel (15% ethyl acetate in hexane) to afford 47 (11.75 g 81%).

G: (9S, 11R, 15S)-11,15-Bis(tetrahydropyran-2-yloxy)-15-cyclohexyl-2,3,4,5,6,16,17,18,19,20decanor-9-(triethylsiloxy)prostanal (48):

To a solution of oxalyl chloride (6.5 g, 51 mmol) in 30 mL of $CH_2Cl_2$ at −78° C. was added dropwise a solution of DMSO (6.7 g, 86 mmol) in 10 mL of $CH_2Cl_2$. After 30 min, a solution of 47 (11.75 g, 17.2 mmol) in 90 mL of $CH_2Cl_2$ was added dropwise. After 6 h, $NEt_3$ (18.9 g, 187 mmol) was added and the reaction was warmed to room temperature. The mixture was added to 150 mL of saturated $NH_4Cl$, the layers were separated, the aqueous layer was extracted with $CH_2Cl_2$ (2×50 mL), the combined organic layers were dried over $MgSO_4$, filtered, and concentrated, and the residue was chromatographed on silica gel (10% ethyl acetate in hexane) to afford aldehyde 48 (8.75 g, 90%).

H: (5Z)-(9S, 11R, 15S)-11,15-Bis(tetrahydropyran-2-yloxy)-15-cyclohexyl-2,3,4,16,17,18,19,20-octanor-9-(triethylsiloxy)-5-prostenoic acid methyl ester (49):

To a mixture of 18-crown-6 (13.1 g, 49.6 mmol), bis(2,2,2-trifluoroethyl) (methoxycarbonylmethyl)phosphonate (7.8 g, 24.6 mmol), and 75 mL of THF at −78° C. was added dropwise a 0.5M solution of KHMDS in toluene (42 mL, 21.5 mmol). After 30 min, a solution of 48 (8.75 g, 15A mmol) in THF (75 mL) was added dropwise. After 2.5 h methanol was added (10 mL), the reaction was warmed to room temperature and added to saturated $NH_4Cl$ (100 mL), the layers were separated, the aqueous layer was extracted with ethyl acetate (2×50 mL), the combined organic layers were dried over $MgSO_4$, filtered, and concentrated, and the residue was chromatographed on silica gel (15% ethyl acetate in hexane) to afford cis-crotonate 49 (4.05 g, 44%), as well as a mixture of cis:trans olefin isomers (2.3 g, 25%).

I: (5Z)-(9S, 11R, 15S)-11,15-Bis(tetrahydropyran-2-yloxy)-15-cyclohexyl-2,3,4,16,17,18,19,20-octanor-9-(triethylsiloxy)-5-prostenol (50):

To a solution of 49 (4.0 g, 6.4 mmol) in 25 mL of THF at 0° C. was added dropwise a 1.5M solution of DIBAL-H in toluene (10 mL, 15 mmol). The reaction was brought to room temperature and stirred overnight. The mixture was added to 75 mL of saturated sodium potassium tartrate and stirred for 30 min, the layers were separated, the aqueous layer was extracted with ethyl acetate (2×50 mL), the combined organic layers were dried over $MgSO_4$, filtered, and concentrated, and the residue was chromatographed on silica gel (20% ethyl acetate in hexane) to provide allyl alcohol 50 (2.84 g, 75%).

J: (5Z)-(9S, 11R, 15S)-11,15-Bis(tetrahydropyran-2-yloxy)-15-cyclohexyl-9-hydroxy-2,3,4,16,17,18,19,20-octanor-5-prostenol (51):

To a solution of 50 (1.7 g, 2.9 mmol) in 20 mL of THF at 0° C. was added a 1M solution of TBAF in THF (4.6 mL, 4.6 mmol). After 30 min 30 mL of saturated $NH_4Cl$ was added, the mixture was extracted with ethyl acetate (3×30 mL), the combined organic layers were dried over $MgSO_4$, filtered, and concentrated, and the residue was chromatographed on silica gel (3/2 ethyl acetate/hexane) to yield diol 51 (1.29 g, 93%).

K: (5Z)-(9S, 11R, 15S)-11,15-Bis(tetrahydropyran-2-yloxy)-15-cyclohexyl-9-hydroxy-3-oxa-16,17,18,19,20pentanor-5-prostenoic acid t-butyl ester (52):

A mixture of 51 (1.29 g, 2.68 mmol), toluene (20 mL), 25% w/w aqueous NaOH (20 mL), $Bu_4NHSO_4$ (175 mg, 0.52 mmol), and t-butyl bromoacetate (2.6 g, 13.5 mmol) was vigorously stirred for 10 min at 0° C. and 45 min at room temperature. The layers were separated, the aqueous layer was extracted with ethyl acetate (2×20 mL), the combined organic layers were dried over $MgSO_4$, filtered, and concentrated, and the residue was chromatographed on silica gel (40% ethyl acetate in hexane) to afford 52 (1.56 g, 98%).

L: (5Z)-(9S, 11R, 15S)-11,15-Bis(tetrahydropyran-2-yloxy)-15-cyclohexyl-9-hydroxy-3-oxa-16,17,18,19,20-pentanor-5-prostenoic acid (53):

A mixture of 52 (2.0 g, 3.4 mmol), lithium hydroxide monohydrate (830 mg, 20 mmol), methanol (20 mL), and water (1 mL) was stirred for 1.5 h, 35 mL of saturated $KH_2PO_4$ was added to adjust the pH to ca. 6, and the mixture was extracted with ethyl acetate (3×25 mL). The combined organic layers were dried over $Na_2SO_4$ filtered, and concentrated to provide crude acid 53, which was used in the next step without purification.

M: (5Z)-(9S, 11R, 15S)-11,15-Bis(tetrahydropyran-2-yloxy)-15-cyclohexyl-9-hydroxy-3-oxa-16,17,18,19,20-pentanor-5-prostenoic acid isopropyl ester (54):

A mixture of 53 from above, acetone (34 mL), isopropyl iodide (2.9 g, 17 mmol), and DBU (3.0 g, 20 mmol) was stirred overnight. The reaction was added to 40 mL of saturated $NH_4Cl$, the mixture was extracted with ethyl acetate (3×25 mL), the combined organic layers were dried over $MgSO_4$, filtered, and concentrated, and the residue was chromatographed on silica gel (1/1 ethyl acetate/hexane) to yield isopropyl ester 54 (1.26 g, 64% from t-butyl ester 52).

N: (5Z)-(9R, 11R, 15S)-11,15-Bis(tetrahydropyran-2-yloxy)-9-chloro-15-cyclohexyl-3-oxa-16,17,18,19,20-pentanor-5-prostenoic acid isopropyl ester (55):

To a solution of 54 (1.26 g, 2.2 mmol) in 13 mL of pyridine at 0° C. was added dropwise methanesulfonyl chloride (600 mg, 5.2 mmol). After 2 h, the mixture was added to a suspension of $Bu_4NCl$ (6.1 g, 21.9 mmol) in toluene (9 mL) and heated at 55°–63° C. for 4 h. After the reaction cooled to room temperature, 30 mL of saturated $NH_4Cl$ was added, the mixture was extracted with ethyl acetate (3 ×30 mL), the combined organic layers were dried over $MgSO_4$, filtered, and concentrated, and the residue was chromatographed on silica gel (20% ethyl acetate in hexane) to provide chlorinated product 55 as a mixture with the corresponding 8,9-olefin (1.07 g, 81% calculated as the chloride). The 8,9-olefin by-product was separated in the next step.

O: (5Z)-(9R, 11R, 15S)-9-Chloro-15-cyclohexyl-11,15-dihydroxy-16,17,18,19,20-pentanor-5-prostenoic acid isopropyl ester (VIII):

The mixture from above containing 55 and the 8,9-olefin (1.07 g, 1.79 mmol, calculated as the chloride) was added to a solution of isopropanol (14 mL), water (1 mL), and 12M HCl (2 mL), and was stirred for 2 h. The reaction was added to 50 mL of saturated NaHCO$_3$, the mixture was extracted with ethyl acetate (3×30 mL), the combined organic layers were dried over MgSO$_4$, filtered, and concentrated, and the residue was purified by radial chromatography (5% isopropanol in toluene) to afford pure VIII (172 mg, 22%), as well as a mixture of containing mostly VIII and a smaller proportion (ca. 30%) of the corresponding 8,9-olefin (333 mg, 42% calculated as the chloride). $^{13}$C NMR (CDCl$_3$) δ 170.21 (C), 131.12 (CH), 127.19 (CH), 76.75 (CH), 75.44 (CH), 68.70 (CH), 67.67 (CH$_2$), 66.78 (CH$_2$), 61.02 (CH), 54.28 (CH), 51.18 (CH), 44.31 (CH$_2$), 44.19 (CH), 31.35 (CH$_2$), 31.19 (CH$_2$), 29.73 (CH$_2$), 29.17 (CH$_2$), 27.60 (CH$_2$), 26.50 (CH), 26.31 (CH), 26.16 (CH$_2$), 21.80 (CH$_3$). CI MS, m/z calcd. for C$_{23}$H$_{40}$O$_5$Cl (MH$^+$) 431, found 431.

EXAMPLE 8

SYNTHESIS OF COMPOUND IX

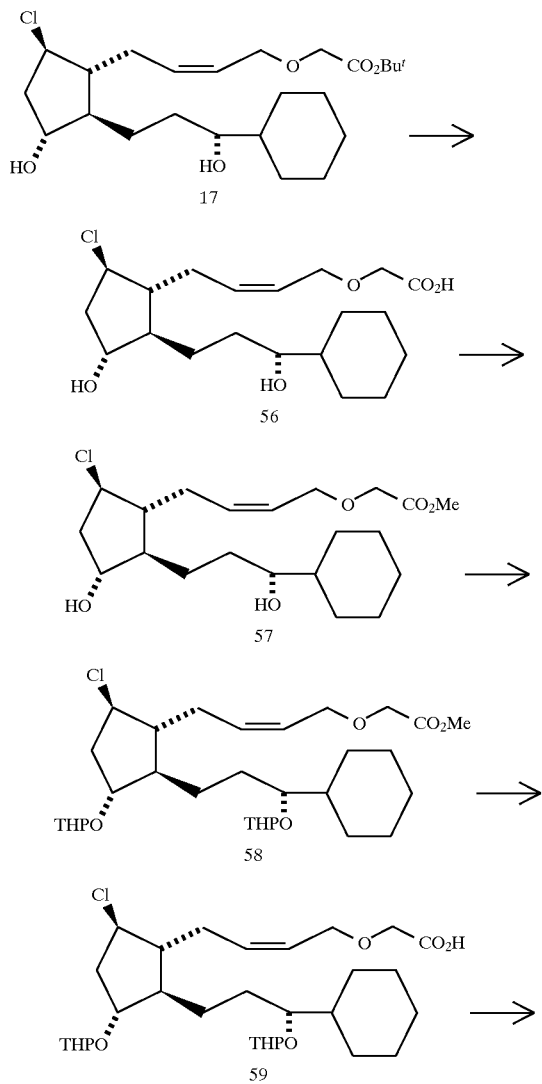

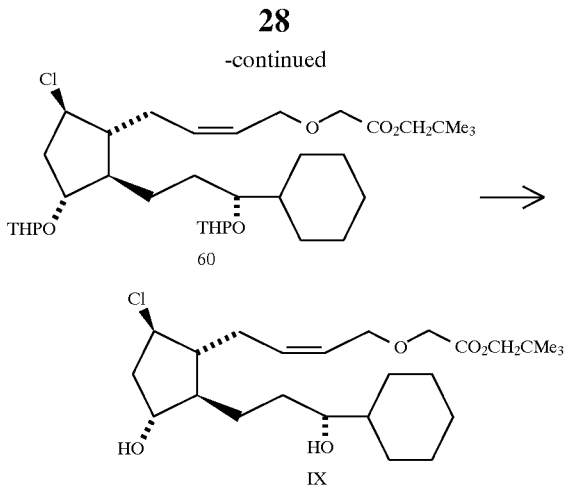

A: (5Z)-(9R, 11R, 15R)-9-Chloro-15-cyclohexyl-11,15-dihydroxy-3-oxa-16,17,18,19,20-pentanor-5-prostenoic acid (56):

To a solution of 32 mg (0.072 mmol) of 17 in a mixture of 2.5 mL of methanol and 1.2 mL of water was added 15 mg (0.36 mmol) of lithium hydroxide monohydrate. After 9 h, 5 mL of 0.1M HCl was added, and the mixture was extracted with CHCl$_3$ (5×5 mL). The combined organic layers were washed with water (20 mL) and brine (20 mL), dried over Na$_2$SO$_4$, filtered, and concentrated to afford 30 mg (100%) of 56 as a colorless oil. $^{13}$C NMR (CDCl$_3$) δ 173.17 (C), 132.77 (CH), 126.03 (CH), 75.68 (CH), 75.24 (CH), 66.89 (CH$_2$), 66.40 (CH$_2$), 61.32 (CH), 54.12 (CH), 50.62 (CH), 43.59 (CH$_2$), 43.33 (CH), 30.92 (CH$_2$), 30.73 (CH$_2$), 29.89 (CH$_2$), 29.30 (CH$_2$), 27.95 (CH$_2$), 26.44 (CH$_2$), 26.25 (CH$_2$), 26.09 (CH$_2$).

B: (5Z)-(9R, 11R, 15R)-9-Chloro-15-cyclohexyl-11,15-dihydroxy-3-oxa-16,17,18,19,20-pentanor-5-prostenoic acid methyl ester (57):

To a solution of 56 (22 mg, 0.057 mmol) in 20 mL of ether was added excess diazomethane as a solution in ether. After 20 min residual diazomethane was removed from solution by a stream of N$_2$ and the solution was concentrated. The residue was chromatographed on silica gel (40% ethyl acetate in hexane) to afford 57 (21 mg, 91%). $^{13}$C NMR (CDCl$_3$) δ 171.06 (C), 131.75 (CH), 126.74 (CH), 75.73 (CH), 75.47 (CH), 67.34 (CH$_2$), 66.77 (CH$_2$), 61.08 (CH), 54.19 (CH), 51.94 (CH$_3$), 51.29 (CH), 44.47 (CH$_2$), 43.62 (CH), 31.49 (CH$_2$), 30.03 (CH$_2$), 29.30 (CH$_2$), 27.98 (CH$_2$), 26.49 (CH$_2$), 26.28 (CH$_2$), 26.13 (CH$_2$).

C: (5Z)-(9R, 11R, 15R)-11,15-Bis(tetrahydropyran-2-yloxy)-9 chloro-15-cyclohexyl-3-oxa-16,17,18,19,20-pentanor-5-prostenoic acid methyl ester (58):

To a mixture of diol 57 (645 mg, 0.65 mmol), DHP (0.56 mL, 6.4 mmol), and CH$_2$Cl$_2$ (10 mL) at 0° C. was added pTSA (10 mg, 0.053 mmol). After 15 min, 15 mL of saturated NaHCO$_3$ was added, the layers were separated, the aqueous layer was extracted with CH$_2$Cl$_2$ (3×15 mL), the combined organic layers were dried over MgSO$_4$, filtered, and concentrated, and the residue was chromatographed on silica gel (30% ethyl acetate in hexane) to afford 781 mg (86%) of bis-THP ether 58.

D: (5Z)-(9R, 11R, 15R)-11,15-Bis(tetrahydropyran-2-yloxy)-9 chloro-15-cyclohexyl-3-oxa-16,17,18,19,20-pentanor-5-prostenoic add (59):

A solution of 58 (342 mg, 0.65 mmol) and lithium hydroxide monohydrate (96 mg, 2.3 mmol) in methanol (20 mL) was stirred for 2 h, the pH of the solution was adjusted to pH 6 with saturated KH$_2$PO$_4$, and the mixture was extracted with CH₂Cl₂ (6×20 mL). The combined organic layers were dried over Na₂SO₄, filtered, and concentrated to afford acid 59 (334 mg, 92%).

E: (5Z)-(9R, 11R, 15R)-11,15-Bis(tetrahydropyran-2-yloxy)-9-chloro-15-cyclohexyl-3-oxa-16,17,18,19,20-pentanor-5-prostenoic acid neopentyl ester (60):

A mixture of 59 (80 mg, 0.14 mmol), dicyclohexylcarbodiimide (30 mg, 0.18 mmol), DMAP (8 mg, 0.07 mmol), 2,2-dimethyl-1-propanol (60 mg, 0.7 mmol), and CH₂Cl₂ (1 mL) was stirred for 3 h at room temperature, the solution was concentrated, and the residue was chromatographed on silica gel (20% ethyl acetate in hexane) to provide 60 contaminated with some dicyclohexyl urea (110 mg total). The sample was used in the next reaction without further purification.

F: (5Z)-(9R, 11R, 15R)-9-Chloro-15-cyclohexyl-11,15-dihydroxy-3-oxa-16,17,18,19,20-pentanor-5-prostenoic add neopentyl ester (IX):

The 110 mg sample from above was dissolved in a mixture of methanol (10 mL) and water (1 mL) at 0° C., and 10 drops of 12N HCl was added. After 15 min, the solution was warmed to room temperature for 30 min. The solution was added to CH₂Cl₂ (10 mL), the layers were separated, and the aqueous layer was extracted with CH₂Cl₂ (3×10 mL). The combined organic layers were dried over MgSO₄, filtered, concentrated, and chromatographed on silica gel (1/1 ethyl acetate/hexane) to afford IX (46 mg, 71% from 59). ¹³C NMR (CDCl₃) δ 170.88 (C), 131.82 (CH), 126.72 (CH), 75.68 (CH), 75.23 (CH), 74.20 (CH₂), 67.34 (CH₂), 66.76 (CH₂), 61.23 (CH), 54.24 (CH), 51.19 (CH), 44.43 (CH), 43.65 (CH), 31.44 (CH₂), 31.34 (C), 30.23 (CH₂), 30.09 (CH₂), 29.33 (CH₂), 28.00 (CH₂), 26.50 (CH), 26.37 (CH₃), 26.28 (CH₂), 26.14 (CH₂). CI MS m/z calcd. for C₂₅H₄₄O₅Cl (MH⁺) 459.2877, found 459.2872.

EXAMPLE 9

SYNTHESIS OF COMPOUND X

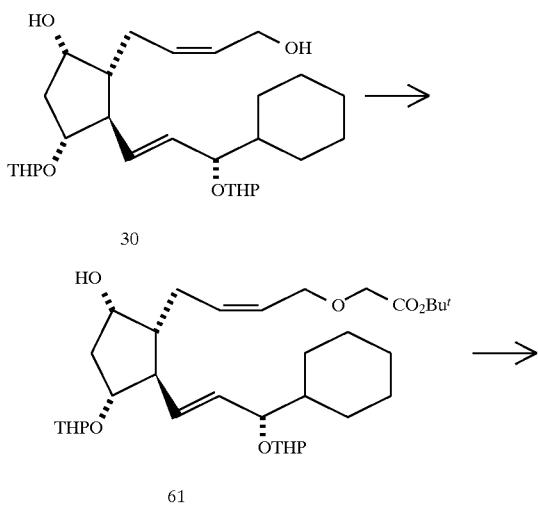

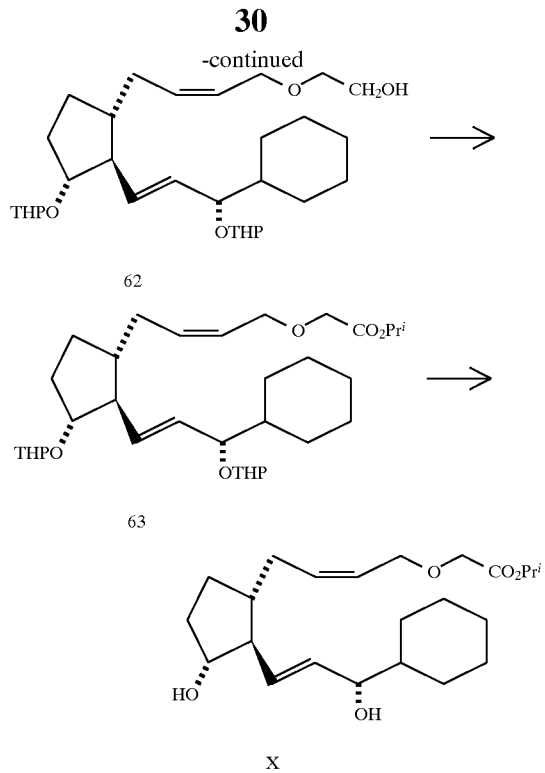

A: (5Z, 13E)-(9S, 11R, 15S)-11,15-Bis(tetrahydropyran-2-yloxy)- 15-cyclohexyl-9-hydroxy-3-oxa- 16,17,18,19,20-pentanor-5,13-prostadienoic acid t-butyl ester (61)

To a vigorously stirring mixture of diol 30 (see Example 3) (925 mg, 1.93 mmol), toluene (25 mL), BrCH₂CO₂But (1.2 g, 6.3 mmol), and Bu4HSO₄ (200 mg, 0.59 mmol) was added 20 mL of a 20% w/w aqueous solution of NaOH. After 40 min the layers were separated, the aqueous layer was extracted with ethyl acetate (2×30 mL), the combined organic layers were dried over MgSO₄, filtered, and concentrated, and the residue was chromatographed on silica gel eluting with 40% ethyl acetate in hexanes to afford 61 (1.10 g, 96%, R$_f$=0.5).

B: (5Z, 13E)-(11R, 15S)-11,15-Bis(tetrahydropyran-2-yloxy-15-cyclohexyl-3-oxa-16,17,18,19,20-pentanor-5, 13-prostadienol (62)

To a mixture of 61 (1.09 g, 1.84 mmol) and pyridine (11 mL) at 0° C. was added dropwise methanesulfonyl chloride (0.51 g, 4.5 mmol). The reaction was stirred at 0° C. for 30 min and for 2 h at room temperature, 40 mL of saturated NH₄Cl was added, and the mixture was extracted with ethyl acetate (2×40 mL). The combined organic layers were dried over MgSO₄, filtered, and concentrated, and the residue was chromatographed on silica gel eluting with 1:1 hexane:ethyl acetate to afford the intermediate 9α-mesylate (1.08 g, 87%, R$_f$=0.5).

To a mixture of the mesylate in THF (11 mL) at 0° C. was added dropwise 1M LiEt₃BH in THF (11 mL, 11 mmol) and the reaction was stirred overnight at room temperature. The mixture was poured into 50 mL of a 1:1 mixture of saturated NH₄Cl:ethyl acetate, the layers were separated, and the aqueous layer was extracted with ethyl acetate (2×30 mL). The combined organic layers were dried over MgSO₄, filtered, and concentrated, and the residue was chromatographed on silica gel eluting with 40% ethyl acetate in hexane to afford 62 (642 mg, 79%, R$_f$=0.4).

C: (5Z, 13E)-(11R, 15S)-11,15-Bis(tetrahydropyran-2-yloxy)- 15-cyclohexyl-3-oxa-16,17,18,19,20-pentanor-5, 13-prostadienoic acid isopropyl ester (63)

To a mixture of 62 (560 mg, 1.12 mmol) and DMF (5 mL) was added pyridinium dichromate (1.32 g, 3.51 mmol). After stirring for 48 h, 20 mL of water was added, and the mixture was extracted with ethyl acetate (4×20 mL). The combined organic layers were filtered and concentrated, the residue was dissolved in acetone (20 mL), and DBU was added (780 mg, 5.12 mmol), followed in 15 min by the addition of isopropyl iodide (850 mg, 5.0 mmol). After 20 h, the reaction was concentrated, and the residue was chromatographed on silica gel eluting with 20% ethyl acetate in hexane to afford 63 (238 mg, 38%, $R_f$=0.4).

D: (5Z, 13E)-(11R, 15S)-15-Cyclohexyl-11,15-dihydroxy-3-oxa-16,17,18,19,20-pentanor-5,13-prostadienoic acid isopropyl ester (X)

To a mixture of 63 (230 mg, 0.41 mmol), isopropanol (18 mL), and water (2 mL) was added 12M HCl (1 mL). After 2 h, 20 mL of saturated $NaHCO_3$ was added, the mixture was extracted with ethyl acetate (3×20 mL), the combined organic layers were dried over $MgSO_4$, filtered, and concentrated, and the residue was chromatographed on silica gel eluting with 3:2 ethyl acetate:hexane to afford X (120 mg, 74%, $R_f$=0.25). $^{13}C$ NMR ($CDCl_3$) δ 170.00 (C), 134.17 (CH), 132.73 (CH), 125.97 (CH), 77.92 (CH), 77.68 (CH), 68.47 (CH), 67.38 ($CH_2$), 66.73 ($CH_2$), 58.02 (CH), 43.44 (CH), 42.77 (CH), 32.15 ($CH_2$), 28.89 ($CH_2$), 28.80 ($CH_2$), 27.63 ($CH_2$), 26.51 ($CH_2$), 26.06 ($CH_2$), 25.94 ($CH_2$), 21.97 ($CH_3$).

The compounds of formula (I) are useful in lowering intraocular pressure and thus are useful in the treatment of glaucoma. The preferred route of administration is topical. The dosage range for topical administration is generally between about 0.001 and about 1000 micrograms per eye (μg/eye) and is preferably between about 0.01 and about 100 μg/eye and most preferably between about 0.05 and 50 μg/eye. The compounds of the present invention can be administered as solutions, suspensions, or emulsions (dispersions) in a suitable ophthalmic vehicle.

In forming compositions for topical administration, the compounds of the present invention are generally formulated as between about 0.00002 to about 0.5 percent by weight (wt %) solutions in water at a pH between about 4.5 and about 8.0. The compounds are preferably formulated as between about 0.0001 to about 0.1 wt % and, most preferably, between about 0.001 and about 0.05 wt %. While the precise regimen is left to the discretion of the clinician, it is recommended that the compositions be topically applied by placing one or more drops in each eye one or more times a day.

Other ingredients which may be desirable to use in the ophthalmic preparations of the present invention include preservatives, co-solvents and viscosity building agents.

Antimicrobial Preservatives:

Ophthalmic products are typically packaged in multidose form, which generally require the addition of preservatives to prevent microbial contamination during use. Suitable preservatives include: benzalkonium chloride, thimerosal, chlorobutanol, methyl paraben, propyl paraben, phenylethyl alcohol, edetate disodium, sorbic acid, ONAMER M®, or other agents known to those skilled in the art. Such preservatives are typically employed at a concentration between about 0.001 and about 1.0 wt %.

Co-Solvents:

Prostaglandins, and particularly ester derivatives, typically have limited solubility in water and therefore may require a surfactant or other appropriate co-solvent in the composition. Such co-solvents include: Polysorbate 20, 60 and 80; Pluronic F-68, F-84 and P-103; Tyloxapol; Cremophor EL; sodium dodecyl sulfate; glycerol; PEG 400; propylene glycol; cyclodextrins; or other agents known to those skilled in the art. Such co-solvents are typically employed at a concentration between about 0.01 and about 2 wt %.

Viscosity Agents:

Viscosity greater than that of simple aqueous solutions may be desirable to increase ocular absorption of the active compound, to decrease variability in dispensing the formulations, to decrease physical separation of components of a suspension or emulsion of formulation and/or otherwise to improve the ophthamic formulation. Such viscosity building agents include: polyvinyl alcohol; polyvinyl pyrrolidone; cellulosic polymers, such as methyl cellulose, hydroxy propyl methylcellulose, hydroxyethyl cellulose, carboxymethyl cellulose, hydroxy propyl cellulose; carboxy vinyl polymers, such as carbomer 910, carbomer 940, carbomer 934P and carbomer 1342; or other agents known to those skilled in the art. Such agents are typically used at a concentration between about 0.01 and about 2 wt %.

EXAMPLE 10

The following Formulations A–D are representative pharmaceutical compositions of the invention for topical use in lowering of intraocular pressure.

Each of Formulations A–D may be formulated in accordance with procedures known to those skilled in the art.

| INGREDIENT | FORMULATION (wt %) | | | |
|---|---|---|---|---|
| | A | B | C | D |
| Compound II | 0.01 | — | — | — |
| Compound III | — | 0.01 | — | — |
| Compound IV | — | — | 0.1 | 0.2 |
| Monobasic Sodium Phosphate | 0.05 | 0.05 | 0.05 | 0.05 |
| Dibasic Sodium Phosphate (anhydrous) | 0.15 | 0.15 | 0.15 | 0.15 |
| Sodium Chloride | 0.75 | 0.75 | 0.5 | 0.6 |
| Disodium EDTA | 0.01 | 0.05 | — | — |
| Cremophor ® EL | — | 0.01 | — | — |
| Hydroxypropyl-β-cyclodextrin | — | — | 4.0 | — |
| Tyloxapol | — | — | — | 0.5 |
| Benzalkonium Chloride | 0.02 | 0.01 | 0.01 | 0.02 |
| Polysorbate 80 | 0.05 | — | — | — |
| HCl and/or NaOH | q.s. to pH 7.3–7.4 | q.s. to pH 7.3–7.4 | q.s. to pH 6.3–6.6 | q.s. to pH 6.3–6.6 |
| Purified Water | q.s. to 100% | q.s. to 100% | q.s. to 100% | q.s. to 100% |

EXAMPLE 11

The ability of certain compounds of the present invention to reduce intraocular pressure (IOP) was evaluated in cynomolgus monkeys with ocular hypertension produced by previous laser trabeculoplasty in the right eye. Animals had been grained to sit in restraint chairs and conditioned to accept experimental procedures without chemical restraint. IOP was determined with a pneumatonometer after light corneal anesthesia with dilute proparacaine.

The two compounds tested are those previously identified as Compound V and Compound VI.

| COMPOUND | PG DOSE | MAXIMUM PERCENT IOP REDUCTION FROM BASELINE |
|---|---|---|
| V | 3 µg | 42 |
| VI | 0.3 µg | 44 |

Compounds V and VI produced significant reduction of intraocular pressure at doses which are marginal or ineffective for other prostaglandins in published clinical studies. By comparison, Nakajima et al. (*Graefe's Arch. Clin. Exp. Ophthalmol.* 229:411–413 (1991)) reported that 50 µg of $PGD_2$ and 2.5 µg of BW245C (a $PGD_2$ analogue) reduce intraocular pressure in human eyes by 12% and 10%, respectively. Other studies (Woodward et al., *Invest. Ophthalmol. Vis. Sci.* 31:138–146 (1990)) reported for these reference compounds in rabbits describe a maximum IOP reduction of approximately 28% for 250 µg of $PGD_2$ and 22% for 25 µg of BW245C. These comparisons indicate the unexpected potency of compounds of the present invention in reducing intraocular pressure. No indications of inflammation were observed during these studies.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method of treating glaucoma and ocular hypertension which comprises topically administering to the affected eye a therapeutically effective amount of a compound of formula:

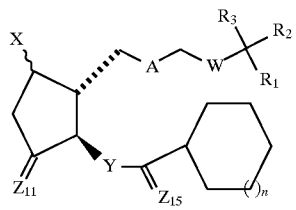

(I)

wherein:

$R_1 = CH_2R$, $CO_2R_4$;

R=OH or functionally modified hydroxy group;

$R_2$ and $R_3$ can be the same or different and are selected from: H and $CH_3$;

$R_4$=H, a cationic salt moiety, substituted or unsubstituted alkyl, cycloalkyl, (cycloalkyl)alkyl, aryl, arylalkyl, heteroaryl, or (heteroaryl)alkyl, wherein substituents include alkyl, halo, a free or functionally modified hydroxy group or a free or functionally modified thiol;

W=$CH_2$, O, S(O)m wherein m=0, 1, 2;

A=$CH_2CH_2$, cis or trans CH=CH, or C≡C;

X=Cl, F or R in either configuration, or H;

$Z_{11}$ and $Z_{15}$ may be the same or different and may be selected from O, or H and R in either configuration;

Y=$CH_2CH_2$ or trans CH=CH, or C≡C; and n=0 or 1;

with the proviso that the following compounds be excluded:

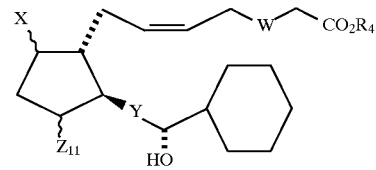

wherein $R_4$ is as defined above;

W=$CH_2$ or O;

X=Cl or F:

Y=$CH_2$ or trans CH=CH;

$Z_{11}$=OH in either configuration, except that if X=F, then $Z_{11}$=OH in the β configuration.

2. The method of claim 1, wherein the compound is of the formula:

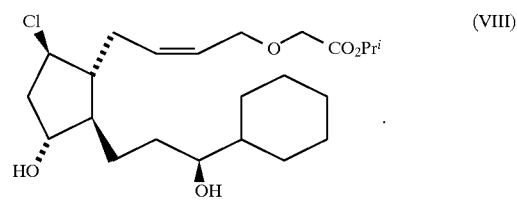

(VIII)

3. The method of claim 1, wherein between about 0.001 and about 1000 micrograms of a compound of formula (I) is administered.

4. The method of claim 3, wherein between about 0.01 and about 100 micrograms of a compound of formula (I) is administered.

5. The method of claim 4, wherein between about 0.05 and about 50 micrograms of a compound of formula (I) is administered.

6. A topical ophthalmic composition for the treatment of glaucoma and ocular hypertension, said composition comprising an ophthalmically acceptable vehicle and a therapeutically effective amount of a compound of formula:

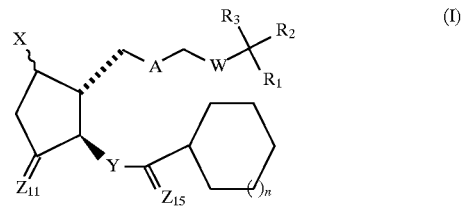

(I)

wherein:

$R_1 = CH_2R$, $CO_2R_4$;

R=OH or functionally modified hydroxy group;

$R_2$ and $R_3$ can be the same or different and are selected from: H and $CH_3$;

$R_4$=H, a cationic salt moiety, substituted or unsubstituted alkyl, cycloalkyl, (cycloalkyl)alkyl, aryl, arylalkyl, heteroaryl, or (heteroaryl)alkyl, wherein substituents include alkyl, halo, a free or functionally modified hydroxy group or a free or functionally modified thiol;

W=$CH_2$, O, $S(O)_m$ wherein m=0, 1, 2;

A=$CH_2CH_2$, cis or trans CH=CH, or C≡C;

X=Cl, F or R in either configuration, or H;

$Z_{11}$ and $Z_{15}$ may be the same or different and may be selected from O, or H and R in either configuration;

Y=$CH_2CH_2$ or trans CH=CH, or C≡C; and n=0 or 1;
with the proviso that the following compounds be excluded:

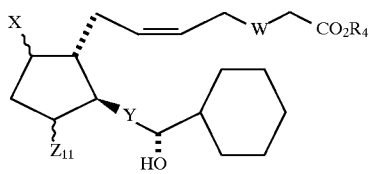

wherein $R_4$ is as defined above;
W=$CH_2$ or O;
X=Cl or F:
Y=$CH_2CH_2$ or trans CH=CH:
$Z_{11}$=OH in either configuration, except that if X=F, then $Z_{11}$=OH in the β configuration.

7. The composition of claim 6, wherein the compound is of formula:

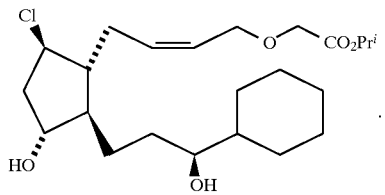

8. The composition of claim 6, wherein the compound of formula (I) is present at a concentration between about 0.00002 and about 0.5 percent by weight.

9. The composition of claim 8, wherein the compound of formula (I) is present at a concentration between about 0.0001 and about 0.1 percent by weight.

10. The composition of claim 9, wherein the compound of formula (I) is present at a concentration between about 0.001 and about 0.05 percent by weight.

11. A compound of formula:

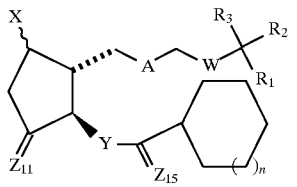

wherein:
$R_1$=$CH_2R$, $CO_2R_4$;
R=OH or functionally modified (i.e., etherified and acylated) hydroxy group;
$R_2$ and $R_3$ can be the same or different and are selected from: H and $CH_3$;
$R_4$=H, a cationic salt moiety, substituted or unsubstituted alkyl, cycloalkyl, (cycloalkyl)alkyl, aryl, arylalkyl, heteroaryl, or (heteroaryl)alkyl, wherein substituents include alkyl, halo, a free or functionally modified hydroxy group or a free or functionally modified thiol;
W=O, $S(O)_m$ wherein m=0, 1, 2;
A=$CH_2CH$, cis or trans CH=CH, or C≡C;
X=H;
$Z_{11}$ and $Z_{15}$ may be the same or different and may be selected from O, or H and R in either configuration;
Y=$CH_2CH_2$ or trans CH=CH, or C≡C; and
n=0 or 1.

12. The compound of claim 11 wherein: $R_1$=$CO_2R_4$; $R_2$ and $R_3$=H; $R_4$=H, a cationic salt moiety, or a substituted or unsubstituted $C_1$–$C_{10}$ alkyl; W=O, A=cis CH=CH; Z=R and H in either configuration; Y=$CH_2CH_2$, or trans CH=CH; $Z_{15}$=H and R in either configuration; and n=0 or 1.

13. The compound of claim 12, having the formula:

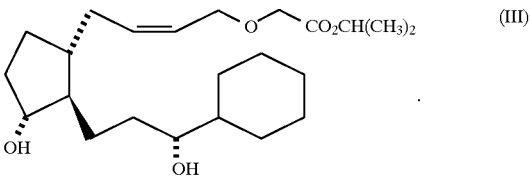

14. The compound of claim 12, having the formula:

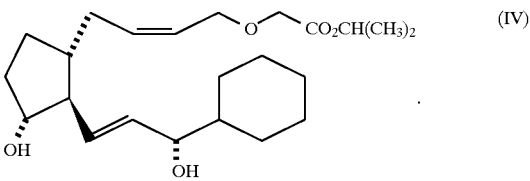

15. A compound having the formula:

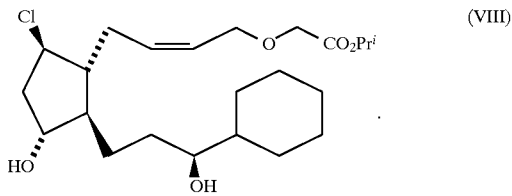

16. The method of claim 1, wherein: $R_2$, $R_3$=H; W=$CH_2$ or O; A is cis CH=CH; X=H; $Z_1$=R in the a configuration and H in the β configuration; Y=$CH_2CH_2$ or trans CH=CH; $Z_{15}$=R and H in either configuration; and n=1.

17. The method of claim 1, wherein: $R_1$=$CH_2R$; $R_2$, $R_3$=H; W=$CH_2$ or O; A=cis CH=CH; X=Cl in the β configuration; $Z_{11}$=R in the a configuration and H in the β configuration; $Z_{15}$=R and H in either configuration; and n=1.

18. The composition of claim 6, wherein: $R_2$, $R_3$=H; W=$CH_2$ or O; A=cis CH=CH; X=H; $Z_{11}$=R in the α configuration and H in the β configuration; Y=$CH_2CH_2$ or trans CH=CH; $Z_{15}$=R and H in either configuration; and n=1.

19. The composition of claim 8, wherein: $R_1$=$CH_2R$; $R_2$, $R_3$=H; W=$CH_2$ or O; A=cis CH=CH; X=Cl in the β configuration; $Z_{11}$=R in the α configuration and H in the β configuration; $Z_{15}$=R and H in either configuration; and n=1.

* * * * *